US012016614B2

(12) United States Patent
Maini

(10) Patent No.: US 12,016,614 B2
(45) Date of Patent: Jun. 25, 2024

(54) DIRECTIONAL BALLOON TRANSSEPTAL INSERTION DEVICE FOR MEDICAL PROCEDURES WITH IMPROVED TRANSSEPTAL PUNCTURE SYSTEM WITH PUNCTURE MEMBER BALLOON SEAL

(71) Applicant: EAST END MEDICAL LLC, Lewes, DE (US)

(72) Inventor: Brijeshwar S. Maini, West Palm Beach, FL (US)

(73) Assignee: EAST END MEDICAL LLC, Miramar, FL (US)

( * ) Notice: Subject to any disclaimer, the term of this patent is extended or adjusted under 35 U.S.C. 154(b) by 775 days.

(21) Appl. No.: 17/025,293

(22) Filed: Sep. 18, 2020

(65) Prior Publication Data

US 2021/0085384 A1   Mar. 25, 2021

Related U.S. Application Data

(60) Provisional application No. 62/903,261, filed on Sep. 20, 2019.

(51) Int. Cl.
*A61B 17/00*   (2006.01)
*A61B 18/14*   (2006.01)
(Continued)

(52) U.S. Cl.
CPC   *A61B 18/1477* (2013.01); *A61B 2017/00247* (2013.01); *A61B 17/3478* (2013.01);
(Continued)

(58) Field of Classification Search
CPC ............ A61B 18/1477; A61B 18/1492; A61B 17/3478; A61B 17/3496; A61B 2018/144;
(Continued)

(56) References Cited

U.S. PATENT DOCUMENTS 4,696,304 A   9/1987   Chin
4,813,934 A   3/1989   Engelson et al.
(Continued)

FOREIGN PATENT DOCUMENTS

AU   2017346559 A1   5/2019
AU   2018307956 A1   2/2020
(Continued)

OTHER PUBLICATIONS

International Search Report and Written Opinion dated Jan. 13, 2021, from PCT/US2020/53902, 12 sheets.
(Continued)

*Primary Examiner* — Linda C Dvorak
*Assistant Examiner* — Davina E. Lee
(74) *Attorney, Agent, or Firm* — FisherBroyles LLP; Anthony J DoVale

(57) ABSTRACT

The disclosed invention provides a transseptal insertion device which is suitable for facilitating precise and safe transseptal puncture of a cardiac interatrial septum. The transseptal insertion device includes a sheath that defines at least one lumen therein, one or more positioning balloons that are connected to a distal end of the sheath, a puncture member movably positioned within the at least one lumen, and a puncture member balloon located on the puncture member. The positioning balloons are inflated and deflated through hypotubes, and the puncture member balloon is inflated and deflated through an additional tube. The transseptal insertion device includes a wire member movably positioned in a center lumen formed in the puncture member. The wire member may be Brockenbrough needle, a radiofrequency tip needle, a radiofrequency wire, a pigtail catheter that delivers fluid or pharmaceuticals in the left atrial appendage, or a transseptal wire.

12 Claims, 32 Drawing Sheets

(51) Int. Cl.
  *A61B 17/34* (2006.01)
  *A61M 25/00* (2006.01)
  *A61M 25/01* (2006.01)
  *A61M 25/10* (2013.01)

(52) U.S. Cl.
  CPC .... *A61B 2018/144* (2013.01); *A61M 25/0068* (2013.01); *A61M 25/0155* (2013.01); *A61M 2025/1061* (2013.01)

(58) Field of Classification Search
  CPC .. A61B 2018/0022; A61B 2018/00247; A61B 8/0883; A61B 2017/00247; A61M 25/0082; A61M 25/0155; A61M 25/1002; A61M 25/1011
  See application file for complete search history.

(56) References Cited

U.S. PATENT DOCUMENTS

| | | |
|---|---|---|
| 5,135,001 A | 8/1992 | Sinofsky et al. |
| 5,295,958 A | 3/1994 | Shturman |
| 5,471,988 A | 12/1995 | Fujio |
| 5,699,805 A | 12/1997 | Seward et al. |
| 5,792,118 A | 8/1998 | Kurth et al. |
| 5,865,801 A | 2/1999 | Houser |
| 6,017,323 A | 1/2000 | Chee |
| 6,102,907 A | 8/2000 | Smethers |
| 6,102,926 A | 8/2000 | Tartaglia et al. |
| 6,129,672 A | 10/2000 | Seward et al. |
| 6,231,588 B1 | 5/2001 | Zadno-Azizi |
| 6,440,097 B1 | 8/2002 | Kupiecki |
| 6,540,712 B1 | 4/2003 | Parodi et al. |
| 7,666,203 B2* | 2/2010 | Chanduszko ...... A61B 17/3468 128/898 |
| 7,678,081 B2 | 3/2010 | Whiting et al. |
| 8,096,959 B2* | 1/2012 | Stewart ............ A61B 17/00234 607/128 |
| 8,900,214 B2 | 12/2014 | Nance et al. |
| 9,072,872 B2 | 7/2015 | Asleson et al. |
| 9,510,904 B2 | 12/2016 | Krishnan |
| 9,545,265 B2 | 1/2017 | Maisano et al. |
| 9,700,351 B2 | 7/2017 | Maisano et al. |
| 9,757,137 B2 | 9/2017 | Krolik et al. |
| 2003/0019546 A1 | 1/2003 | Kanekiyo et al. |
| 2003/0023204 A1 | 1/2003 | Vo et al. |
| 2003/0229386 A1 | 12/2003 | Rosenman et al. |
| 2004/0215233 A1 | 10/2004 | Kaplan |
| 2005/0065419 A1 | 3/2005 | Partridge et al. |
| 2005/0159738 A1 | 7/2005 | Visram et al. |
| 2005/0197530 A1 | 9/2005 | Wallace |
| 2005/0245822 A1 | 11/2005 | Dala-Krishna et al. |
| 2006/0009715 A1 | 1/2006 | Khairkhahan et al. |
| 2007/0149995 A1* | 6/2007 | Quinn ............ A61B 17/12136 604/101.04 |
| 2007/0270751 A1 | 11/2007 | Stangenes et al. |
| 2007/0293724 A1 | 12/2007 | Saadat et al. |
| 2008/0132937 A1 | 6/2008 | Hartley |
| 2008/0171989 A1 | 7/2008 | Bell |
| 2008/0243081 A1 | 10/2008 | Nance |
| 2008/0262596 A1 | 10/2008 | Xiao |
| 2009/0076498 A1 | 3/2009 | Saadat et al. |
| 2009/0259272 A1 | 10/2009 | Reddy et al. |
| 2010/0010488 A1 | 1/2010 | Kassab |
| 2010/0036410 A1 | 2/2010 | Krolik |
| 2010/0168777 A1 | 7/2010 | Stangenes et al. |
| 2010/0174189 A1 | 7/2010 | Abraham |
| 2010/0204561 A1 | 8/2010 | Saadat |
| 2010/0286718 A1 | 11/2010 | Kassab |
| 2011/0270239 A1 | 11/2011 | Werneth |
| 2011/0295268 A1 | 12/2011 | Roelle |
| 2012/0203169 A1 | 8/2012 | Tegg |
| 2012/0259263 A1 | 10/2012 | Celermajer |
| 2013/0090649 A1* | 4/2013 | Smith ............ A61B 18/1492 606/41 |
| 2013/0102862 A1 | 4/2013 | Mercader |
| 2014/0039494 A1 | 2/2014 | Kick et al. |
| 2014/0081301 A1* | 3/2014 | Tran .............. A61N 7/022 606/169 |
| 2014/0155980 A1 | 6/2014 | Turjman |
| 2014/0171903 A1 | 6/2014 | Roman et al. |
| 2014/0276027 A1 | 9/2014 | Gaddis |
| 2014/0309675 A1* | 10/2014 | Maisano ........... A61B 17/3478 606/170 |
| 2015/0165170 A1 | 6/2015 | Beasley |
| 2015/0173794 A1 | 6/2015 | Kurth et al. |
| 2015/0216620 A1 | 8/2015 | Davies et al. |
| 2015/0217093 A1 | 8/2015 | Tsutsui |
| 2015/0224240 A1 | 8/2015 | Farnan et al. |
| 2015/0258270 A1 | 9/2015 | Kunis |
| 2015/0306359 A1 | 10/2015 | Drasler |
| 2016/0008636 A1 | 1/2016 | Warnking |
| 2016/0051321 A1 | 2/2016 | Salahieh et al. |
| 2016/0081704 A1 | 3/2016 | Jeon et al. |
| 2016/0100860 A1 | 4/2016 | Lenker et al. |
| 2016/0143522 A1 | 5/2016 | Ransbury et al. |
| 2016/0193449 A1 | 7/2016 | Sarabia et al. |
| 2016/0220793 A1* | 8/2016 | Murphy ............. H03M 13/271 |
| 2016/0279393 A1 | 9/2016 | Anderson et al. |
| 2017/0105761 A1 | 4/2017 | Sapir |
| 2017/0135559 A1* | 5/2017 | Horrisberger ........ A61B 1/3137 |
| 2017/0143940 A1 | 5/2017 | Flygare |
| 2018/0103985 A1 | 4/2018 | Maini |
| 2018/0177516 A1 | 6/2018 | Vardi |
| 2018/0264231 A1 | 9/2018 | Scheibe et al. |
| 2019/0000544 A1 | 1/2019 | Govari et al. |
| 2019/0029722 A1 | 1/2019 | Maini |
| 2019/0029750 A1 | 1/2019 | Maini |
| 2019/0134412 A1 | 5/2019 | Shuros et al. |
| 2019/0209177 A1 | 7/2019 | Whitfield et al. |
| 2020/0297412 A1 | 9/2020 | Maini |
| 2020/0390495 A1 | 12/2020 | Maini |
| 2021/0085384 A1 | 3/2021 | Maini |
| 2021/0100981 A1 | 4/2021 | Maini |
| 2021/0251553 A1 | 8/2021 | Maini |

FOREIGN PATENT DOCUMENTS

| | | |
|---|---|---|
| AU | 2018307969 A1 | 2/2020 |
| AU | 2020241992 A1 | 10/2021 |
| AU | 2020292273 A1 | 1/2022 |
| AU | 2020349508 A1 | 4/2022 |
| AU | 2020357991 A1 | 4/2022 |
| CA | 3041032 A1 | 4/2018 |
| CA | 3071391 A1 | 1/2019 |
| CA | 3071432 A1 | 1/2019 |
| CA | 3138742 A1 | 9/2020 |
| CA | 3141251 A1 | 12/2020 |
| CA | 3151548 A1 | 3/2021 |
| CA | 3153126 A1 | 4/2021 |
| CL | 2019001078 A1 | 11/2019 |
| CL | 2020000232 A1 | 2/2021 |
| CN | 1599579 A | 3/2005 |
| CN | 101442946 A | 5/2009 |
| CN | 103429179 A | 12/2013 |
| CN | 107530532 A | 1/2018 |
| CN | 110022779 A | 7/2019 |
| CN | 111093539 A | 5/2020 |
| CN | 111148474 A | 5/2020 |
| CN | 113692257 A | 11/2021 |
| CN | 114269270 A | 4/2022 |
| CN | 114727804 A | 7/2022 |
| CN | 110022779 B | 8/2022 |
| CN | 114980824 A | 8/2022 |
| EP | 2233169 A1 | 9/2010 |
| EP | 2459266 A1 | 6/2012 |
| EP | 3528711 A1 | 8/2019 |
| EP | 3528711 A4 | 6/2020 |
| EP | 3658036 A1 | 6/2020 |
| EP | 3658045 A1 | 6/2020 |
| EP | 3941371 A1 | 1/2022 |
| EP | 3982849 A1 | 4/2022 |
| EP | 4037585 A1 | 8/2022 |
| EP | 3253438 B1 | 9/2022 |

(56) References Cited

FOREIGN PATENT DOCUMENTS

| | | |
|---|---|---|
| IN | 201917018712 A | 8/2019 |
| IN | 202017008571 A | 8/2020 |
| IN | 202017008345 A | 10/2020 |
| IN | 202217000583 A | 3/2022 |
| IN | 202217016718 A | 7/2022 |
| IN | 202117041934 A | 9/2022 |
| IN | 202217020063 A | 9/2022 |
| JP | H06506853 | 8/1994 |
| JP | 1994066638 | 9/1994 |
| JP | H08117232 A | 5/1996 |
| JP | 2009539575 | 11/2009 |
| JP | 2013226429 A | 11/2013 |
| JP | 2019531829 A | 11/2019 |
| JP | 2020530372 A | 10/2020 |
| JP | 2020530373 A | 10/2020 |
| JP | 2022527456 A | 6/2022 |
| JP | 7113820 B2 | 8/2022 |
| JP | 2022536719 A | 8/2022 |
| WO | 02/096264 A2 | 12/2002 |
| WO | 2007147060 A2 | 12/2007 |
| WO | 2014036317 A2 | 3/2014 |
| WO | 2015058007 A1 | 4/2015 |
| WO | 2015200518 A1 | 12/2015 |
| WO | 2017083785 | 5/2017 |
| WO | 2018033401 A1 | 2/2018 |
| WO | 2018075426 A1 | 4/2018 |
| WO | WO-2018175743 A1 * 9/2018 ....... A61B 17/00234 |
| WO | 2019023609 A1 | 1/2019 |
| WO | 2019023653 A1 | 1/2019 |
| WO | 2019113043 A1 | 6/2019 |
| WO | 2019023653 A8 | 8/2019 |
| WO | 2020191133 A1 | 9/2020 |
| WO | 2020251999 A1 | 12/2020 |
| WO | 2021055572 A1 | 3/2021 |
| WO | 2021067669 A1 | 4/2021 |

OTHER PUBLICATIONS

Non-Final Office Action dated Jan. 26, 2021, from U.S. Appl. No. 15/784,792, 41 sheets.
International Search Report and Written Opinion for International Application No. PCT/US2018/044143 dated Dec. 5, 2018, 16 sheets.
International Search Report and Written Opinion for International Application No. PCT/US2018/044207 dated Oct. 31, 2018, 17 sheets.
International Search Report and Written Opinion for International Application No. PCT/US2020/023518 dated Jun. 23, 2020, 15 sheets.
The extended European search report dated May 12, 2020, from EP Application No. 17862286.6, 8 sheets.
International Search Report and Written Opinion dated Dec. 14, 2017, from PCT/US2017/056843, 10 sheets.
Non-Final Office Action dated Feb. 6, 2020, from U.S. Appl. No. 15/784,792, 29 sheets.
Final Office Action dated Aug. 4, 2020, from U.S. Appl. No. 15/784,792, 38 sheets.
International Search Report and Written Opinion for International Application No. PCT/US2020/036965 dated Sep. 16, 2020, 16 sheets.
First Office Action dated May 7, 2021, from Chinese Application No. 201780074077.5, 15 sheets.
Written Opinion dated Jun. 16, 2021, from Chilean Patent Application No. 202000403, 16 sheets.
International Search Report and Written Opinion dated May 25, 2021, from International Patent Application No. PCT/US2021/017528, 15 sheets.
International Search Report and Written Opinion for International Application No. PCT/US2020/051228 dated Dec. 1, 2020, 14 sheets.
EP Application No. 18756031.3, EP Communication dated Oct. 4, 2021, 11 pages.
International Preliminary Report on Patentability PCT/US2017/056843; dated May 2, 2019, 5 pages.
International Preliminary Report on Patentability PCT/US2018/044143; dated Feb. 28, 2020, 9 pages.
International Preliminary Report on Patentability PCT/US2018/044207; dated Feb. 6, 2020, 8 pages.
International Preliminary Report on Patentability PCT/US2020/023518; dated Sep. 30, 2021, 10 pages.
International Preliminary Report on Patentability PCT/US2020/036965; dated Dec. 23, 2021, 8 pages.
International Preliminary Report on Patentability PCT/US2020/051228; dated Mar. 31, 2022, 9 pages.
International Preliminary Report on Patentability PCT/US2020/053902; dated Apr. 14, 2022, 5 pages.
Final Office Action dated Aug. 18, 2021, from U.S. Appl. No. 15/784,792, 55 sheets.
Communication Pursuant to Article 94(3) EPC dated Aug. 25, 2021, from EP Application No. 18755361.5, 4 sheets.
Office Action dated Sep. 3, 2021, from Chile Application No. 202000232, 20 sheets.
Notice of Reasons for Rejection dated Sep. 28, 2021, from Japanese Application No. 2019-521811, 4 sheets.
International Search Report and Written Opinion dated Oct. 1, 2021, from PCT Application No. PCT/US2021/018409, 17 sheets.
Final Office Action dated Oct. 7, 2021, from U.S. Appl. No. 16/047,910, 29 sheets.
Office Action dated Oct. 6, 2021, U.S. Appl. No. 16/048,005, 81 sheets.
Non-Final Office Action dated Apr. 30, 2021, from U.S. Appl. No. 16/047,910, 46 sheets.
Invitation to Respond to Written Opinion from Singapore Patent Application No. 11202000666S, dated Mar. 2, 2021, 11 sheets.
Invitation to Respond to Written Opinion from Singapore Patent Application No. 11202000667S, dated Mar. 2, 2021, 11 sheets.

* cited by examiner

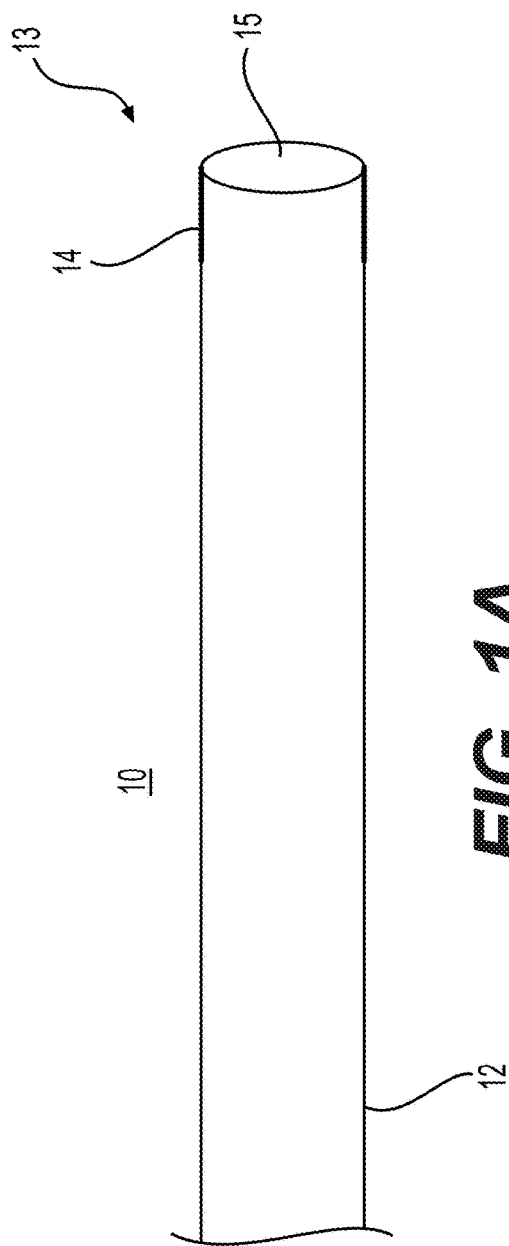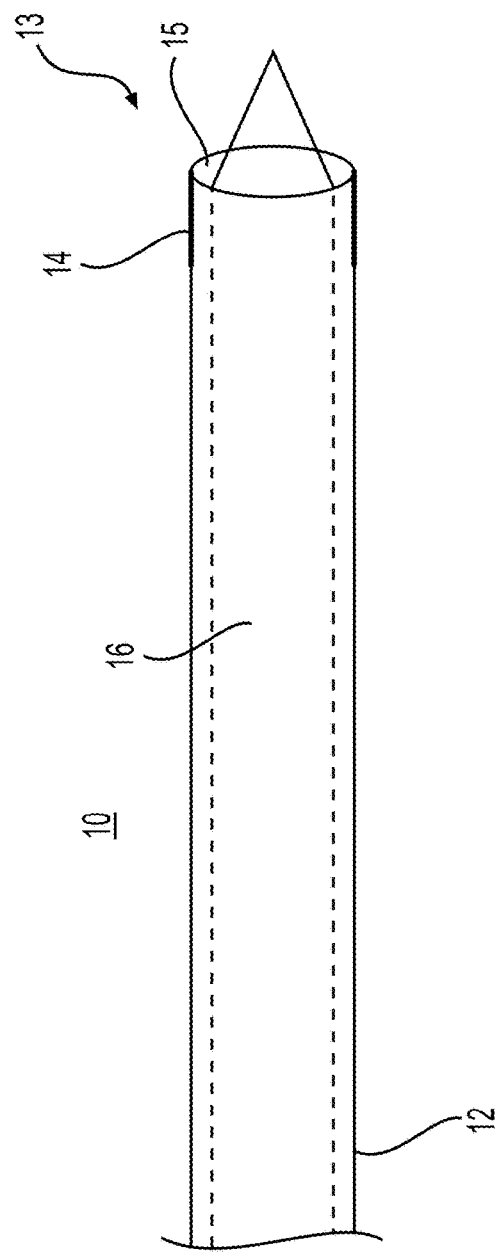

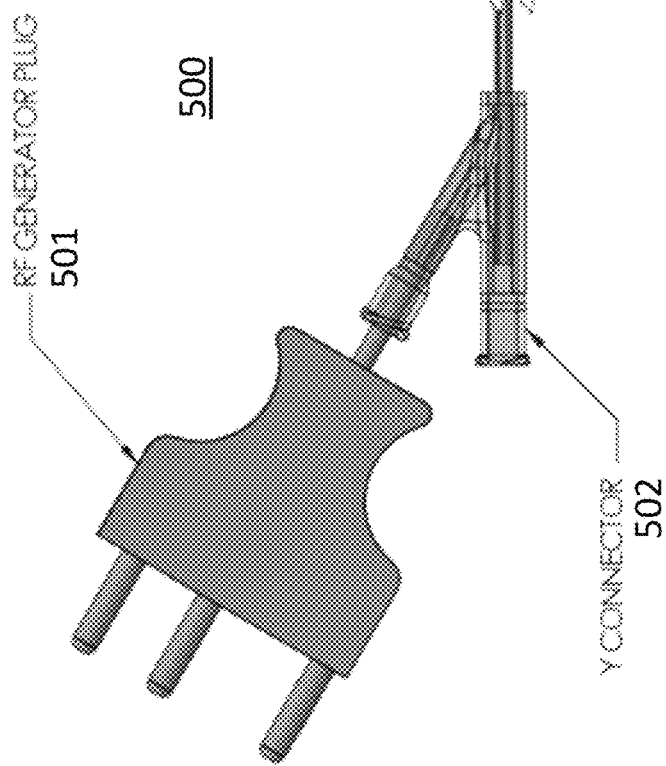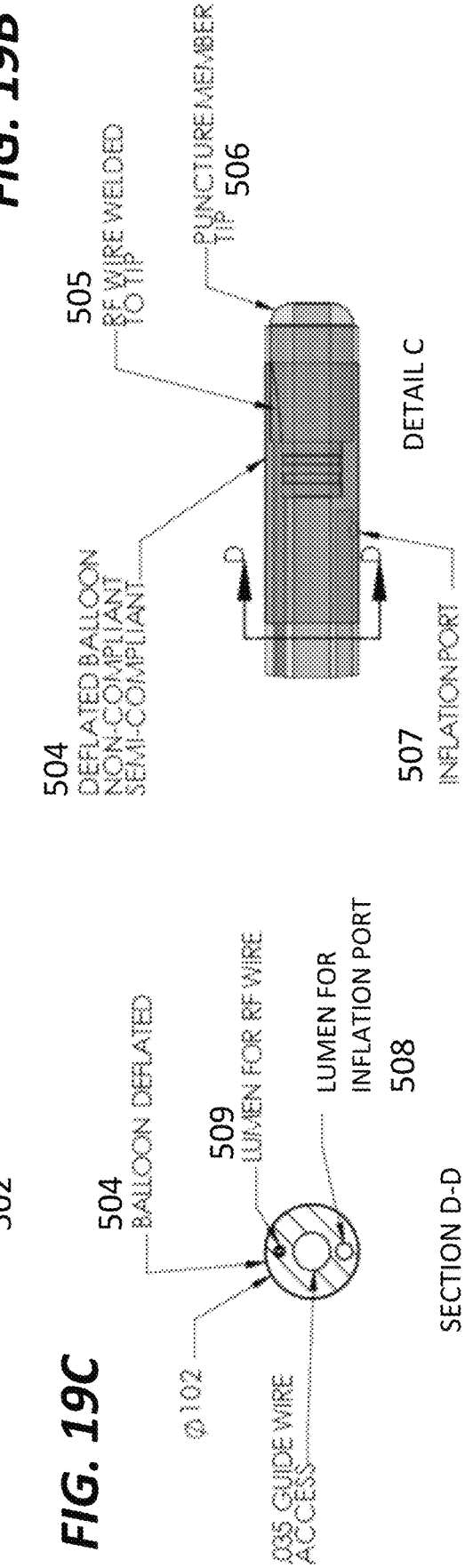

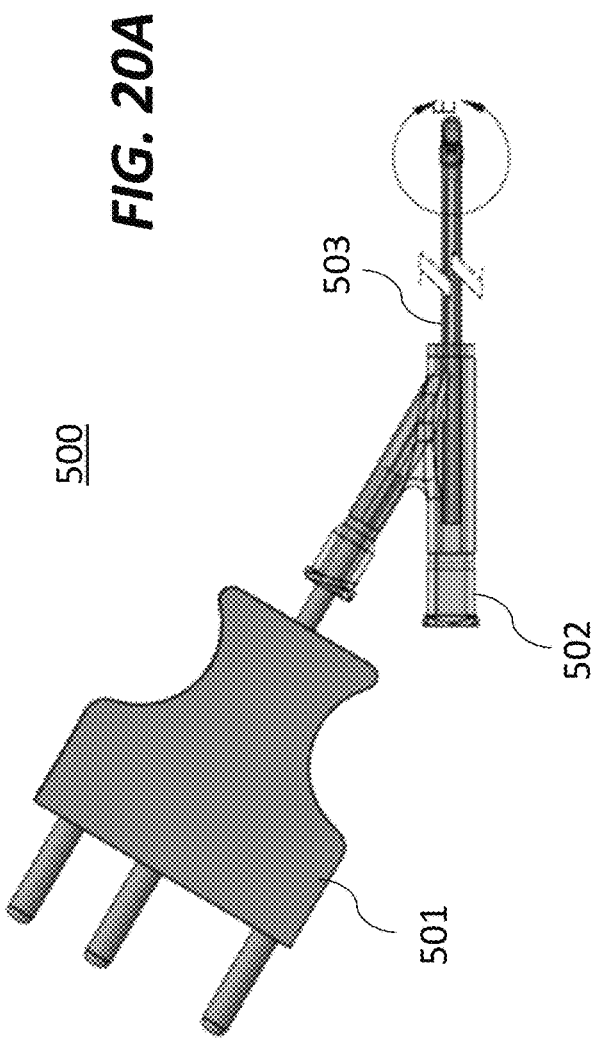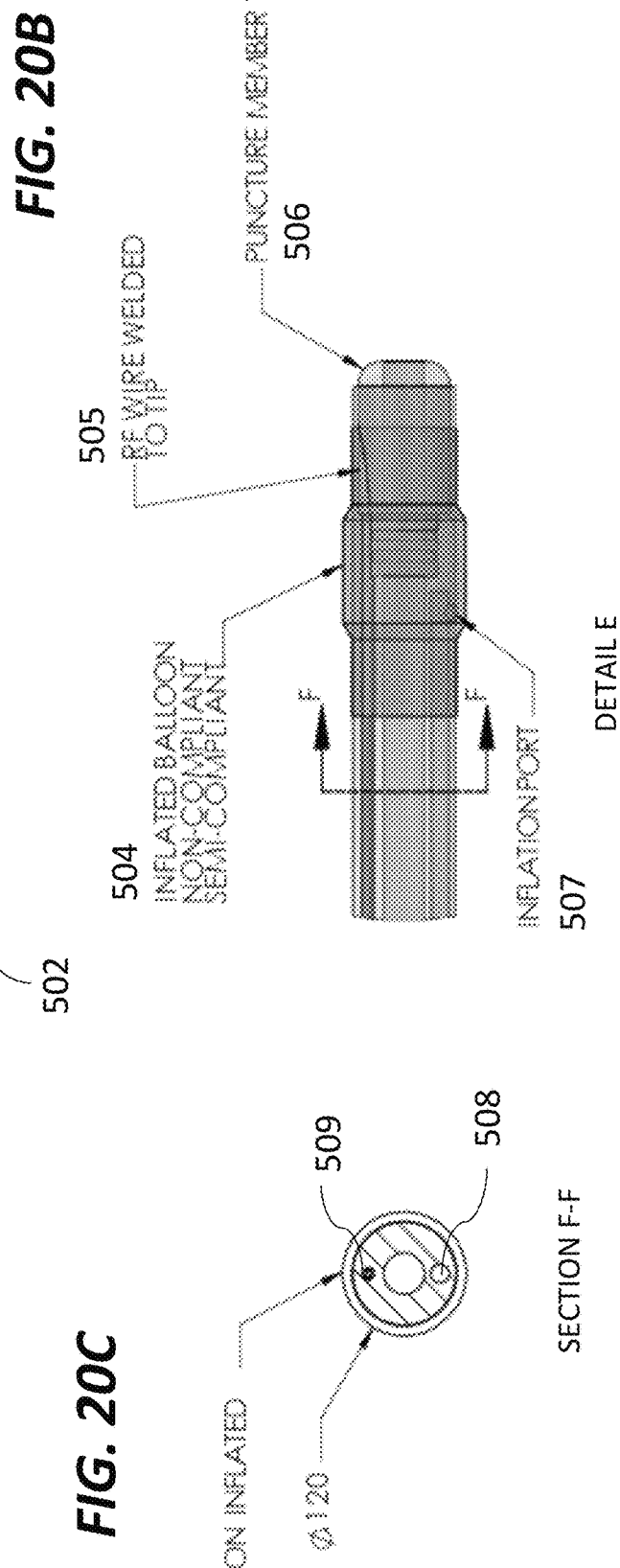

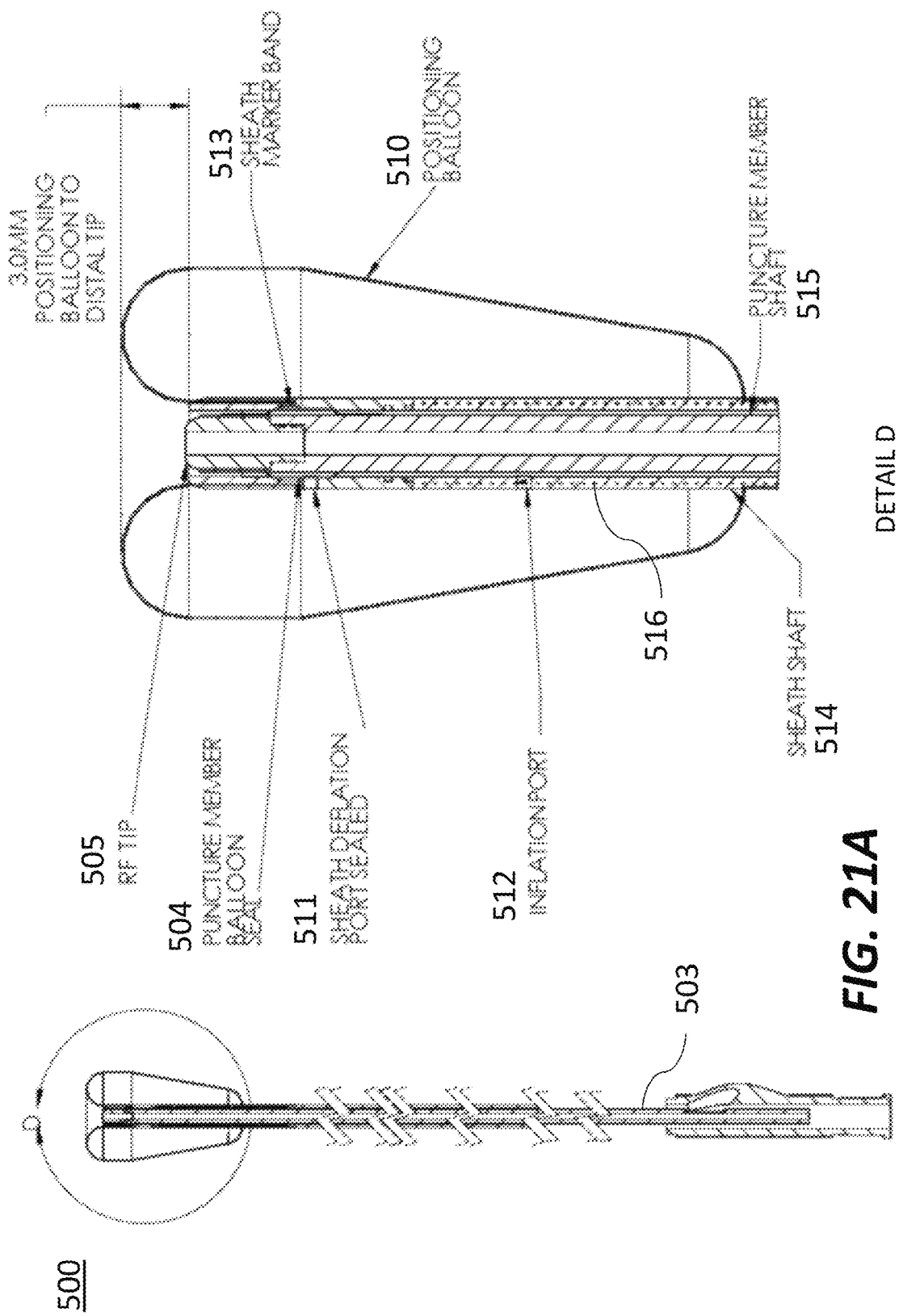

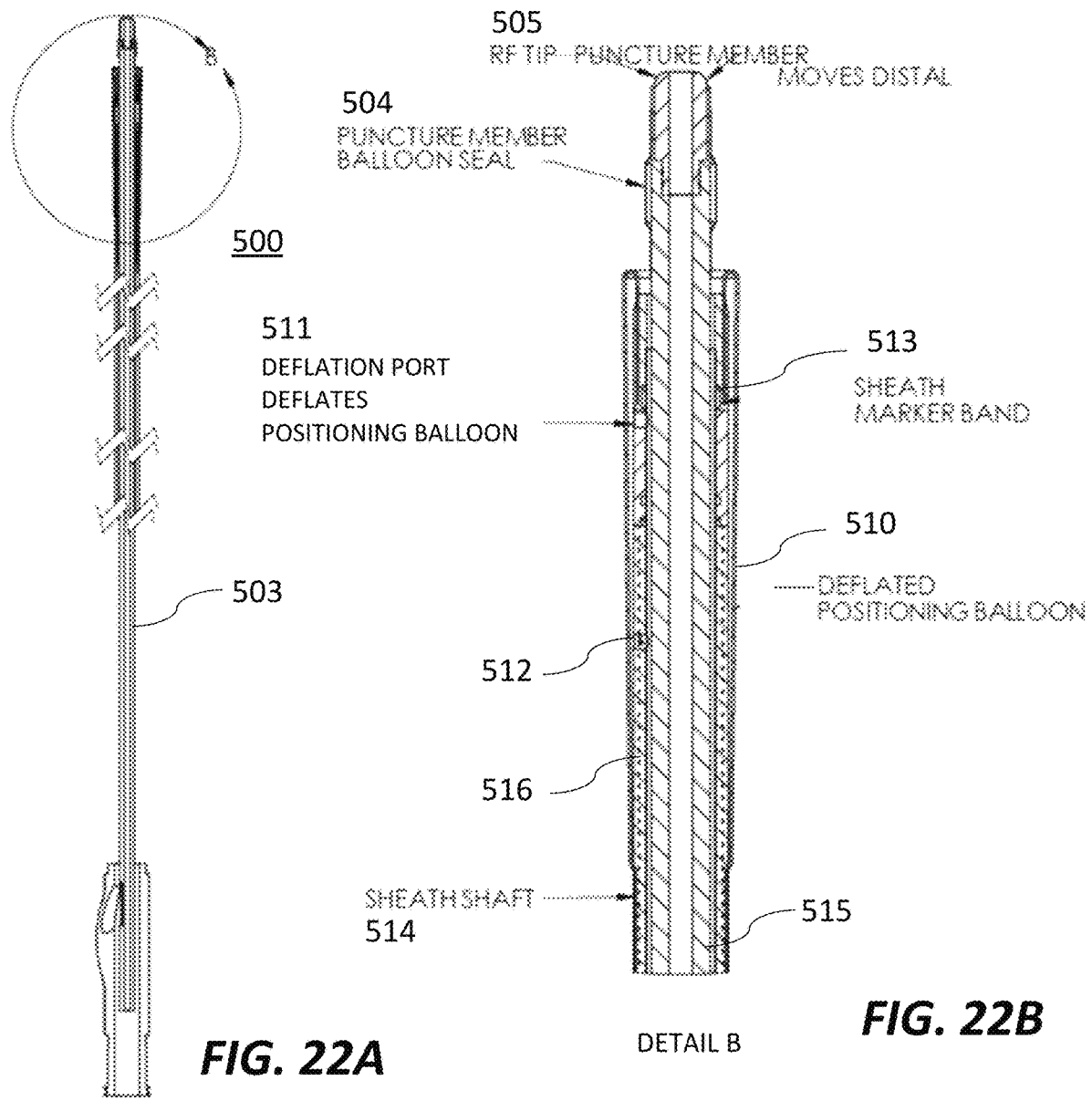

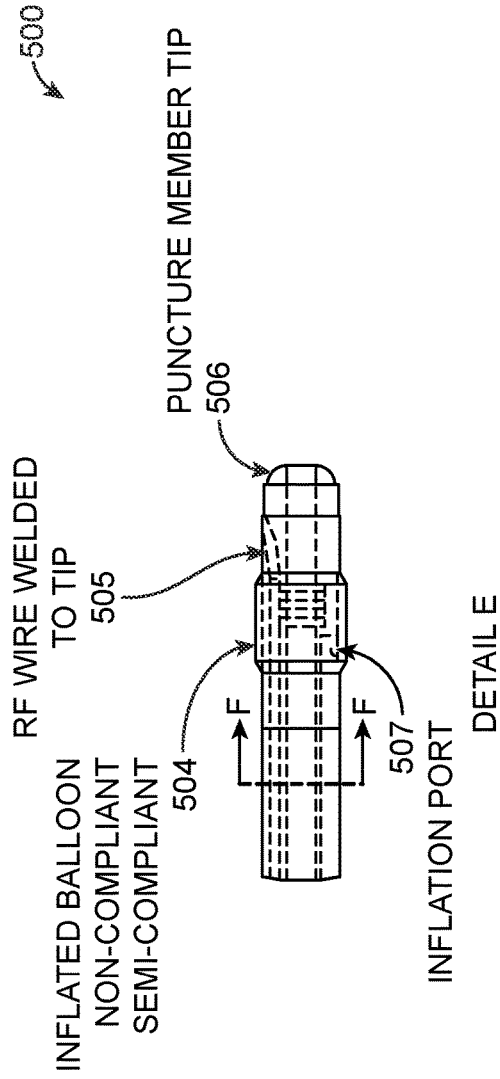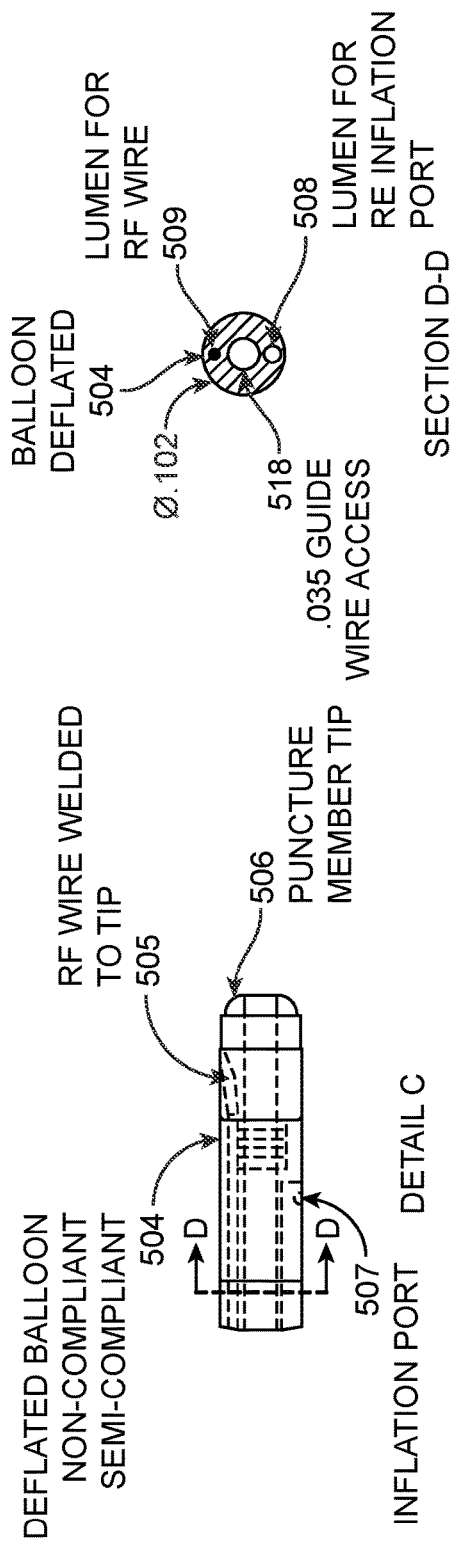

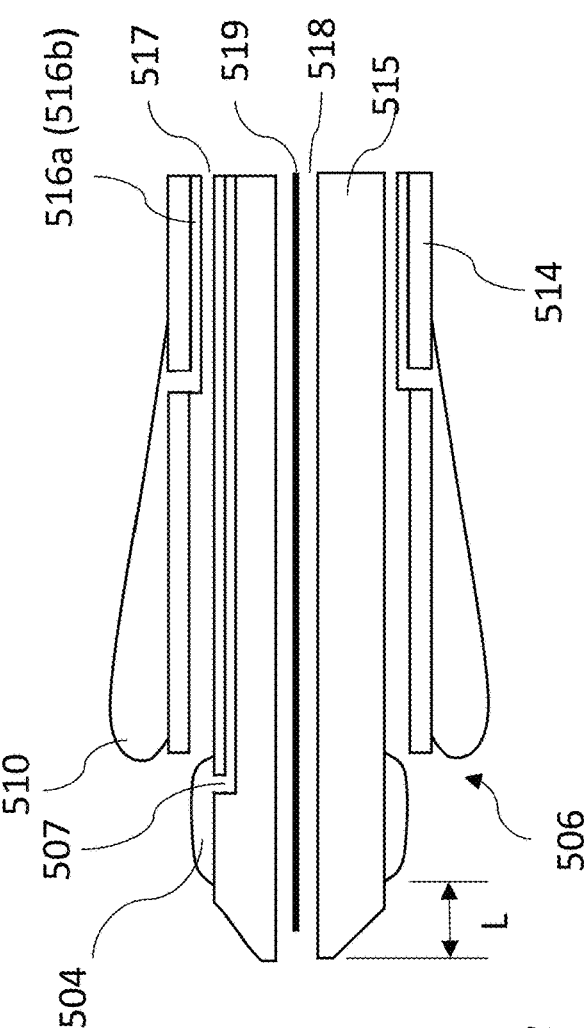
FIG. 25C
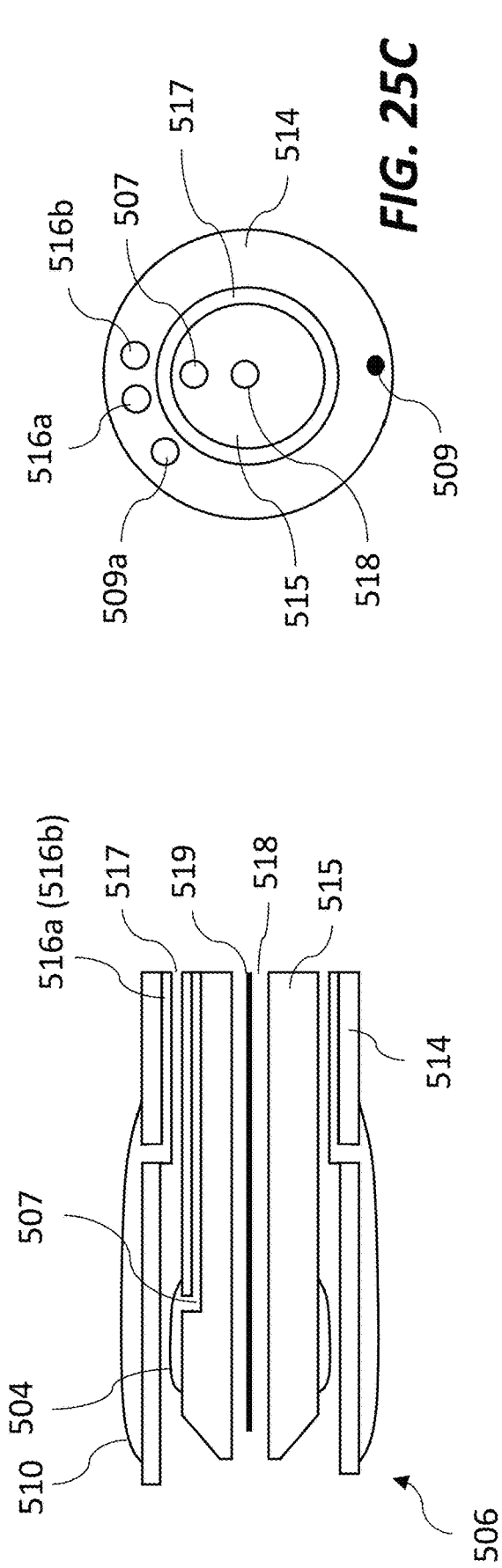
FIG. 25A
FIG. 25B

DIRECTIONAL BALLOON TRANSSEPTAL INSERTION DEVICE FOR MEDICAL PROCEDURES WITH IMPROVED TRANSSEPTAL PUNCTURE SYSTEM WITH PUNCTURE MEMBER BALLOON SEAL

CROSS REFERENCE TO RELATED APPLICATIONS

This application claims the priority of U.S. Provisional Application Ser. No. 62/903,261, filed on Sep. 20, 2019, which is hereby incorporated herein by reference in its entirety.

FIELD

The present invention relates generally to cardiac catheters, and more particularly, to a transseptal insertion device which is suitable for facilitating quick and safe transseptal puncture and insertion of a catheter through a cardiac septum to provide access to the left atrium in implementation of a left atrial intervention.

BACKGROUND

Cardiac catheterization is a medical procedure in which a long thin tube or catheter is inserted through an artery or vein into specific areas of the heart for diagnostic or therapeutic purposes. More specifically, cardiac chambers, vessels and valves may be catheterized.

Cardiac catheterization may be used in procedures such as coronary angiography and left ventricular angiography. Coronary angiography facilitates visualization of the coronary vessels and finding of potential blockages by taking X-ray images of a patient who has received a dye (contrast material) injection into a catheter previously injected in an artery. Left ventricular angiography enables examination of the left-sided heart chambers and the function of the left sided valves of the heart, and may be combined with coronary angiography. Cardiac catheterization can also be used to measure pressures throughout the four chambers of the heart and evaluate pressure differences across the major heart valves. In further applications, cardiac catheterization can be used to estimate the cardiac output, or volume of blood pumped by the heart per minute.

Some medical procedures may require catheterization into the left atrium of the heart. For this purpose, to avoid having to place a catheter in the aorta, access to the left atrium is generally achieved by accessing the right atrium, puncturing the interatrial septum between the left and right atria of the heart, and threading the catheter through the septum and into the left atrium. Transseptal puncture must be carried out with extreme precision, as accidental puncturing of surrounding tissue may cause very serious damage to the heart. In addition, transseptal puncture may require complicated instruments which are not helpful in guaranteeing the precision of the puncture.

The use of devices available today present many challenges for doctors attempting to puncture the interatrial septum and perform cardiac catheterization. Locating the interatrial septum, properly placing the distal end of the puncturing device at the desired location of the septum, safely puncturing the interatrial septum, avoiding accidental punctures, and tracking and maneuvering the catheter post-puncture, are among the many challenges facing those performing cardiac catheterization today.

SUMMARY

Accordingly, there is an established need for a device that is suitable for facilitating quick and safe transseptal puncturing to provide access to the left atrium in implementation of a left atrial intervention.

These advantages and others are achieved, for example, by a transseptal insertion device which is suitable for facilitating precise and safe transseptal puncture of a cardiac interatrial septum. The transseptal insertion device includes a sheath that defines at least one lumen therein, one or more positioning balloons that are connected to the distal end of the sheath, a puncture member movably positioned within the at least one lumen, and a puncture member balloon located on the distal end of the puncture member. The sheath has a distal end that is positioned toward the cardiac interatrial septum of a patient when the transseptal insertion device is in use and a proximal end that is external to the patient. The one or more positioning balloons, when inflated and the transseptal insertion device is in use, overhang and extend past the distal end of the sheath. The sheath includes one or more hypotubes respectively connected to the one or more positioning balloons to inflate and deflate the one or more positioning balloons. The puncture member has a distal end that is positioned toward the cardiac interatrial septum of the patient. The puncture member has a distal end and is designed to and is capable of precisely puncturing the cardiac interatrial septum. The puncture member includes at least one puncture member tube connected to the puncture member balloon to inflate and deflate the puncture member balloon.

The one or more positioning balloons may be inflated by gas or fluid supplied through the one or more hypotubes, and the one or more positioning balloons and the puncture member balloon may be inflated and deflated independently of each other. The one or more hypotubes may include one or more inflation hypotubes to inflate the one or more positioning balloons, and one or more deflation hypotubes to deflate the one or more positioning balloons. The one or more positioning balloons, when inflated, may deliver energy in the form of heat or be used for cryoablation with fluid that is circulated through the one or more positioning balloons. The puncture member balloon, when inflated, may be positioned at a predetermined distance from a tip of the distal end of the puncture member to prevent the puncture member from being pushed beyond the predetermined distance while the puncture member is tenting the cardiac interatrial septum and the puncture member balloon is pressing against the cardiac interatrial septum.

The transseptal insertion device may further include a wire member movably positioned in a center lumen formed in the puncture member. The wire member advances beyond a tip of the distal end of the puncture member when in use. The wire member may be a Brockenbrough needle, a radiofrequency tip needle, a radiofrequency wire, a pigtail catheter that delivers fluid or pharmaceuticals in the left atrial appendage, or a transseptal wire designed to and capable of precisely puncturing the cardiac interatrial septum. The sheath may include a side port proximal to the positioning balloons. An additional catheter or wire advances into the cardiac interatrial septum through the side port and the additional catheter or wire is capable of capturing the wire member.

These advantages and others are also achieved, for example, by a method for suitably facilitating precise and safe transseptal puncture of a cardiac interatrial septum with a transseptal insertion device. The method includes steps of inflating one or more positioning balloons connected to a distal end of a sheath of the transseptal insertion device, advancing a puncture member while the positioning balloons are inflated, positioning the puncture member against the cardiac interatrial septum, deflating the one or more positioning balloons, further advancing the puncture member to puncture the cardiac interatrial septum, and advancing the transseptal insertion device crossing the cardiac interatrial septum. The one or more positioning balloons, when inflated and the transseptal insertion device is in use, overhang and extend past the distal end of the sheath. The sheath includes one or more hypotubes respectively connected to the one or more positioning balloons to inflate and deflate the one or more positioning balloons. The puncture member is movably positioned within at least one lumen of the sheath. A puncture member balloon is located on a distal end of the puncture member and the puncture member includes at least one puncture member tube connected to the puncture member balloon to inflate and deflate the puncture member balloon.

The method may further include steps of inflating the puncture member balloon once the puncture member advances beyond the distal end of the sheath and is tenting the cardiac interatrial septum, and deflating the puncture member balloon before said further advancing the puncture member to puncture the cardiac interatrial septum. The puncture member balloon may be pressing against the cardiac interatrial septum while the puncture member is tenting the cardiac interatrial septum. The method may further include one or more of steps of re-inflating the one or more positioning balloons to navigate in an atraumatic fashion to different parts of the left atrium after the distal end of the transseptal insertion device crosses the cardiac interatrial septum, re-inflating the puncture member balloon to anchor the transseptal insertion device against the cardiac interatrial septum after the distal end of the transseptal insertion device crosses the cardiac interatrial septum, delivering, via the one or more positioning balloons, energy in the form of heat or using the one or more positioning balloons for cryoablation with fluid that is circulated through the one or more positioning balloons, advancing a wire member beyond a tip of the distal end of the puncture member after the distal end of the transseptal insertion device crosses the cardiac interatrial septum where the wire member movably positioned in a center lumen formed in the puncture member, advancing an additional catheter or wire into the cardiac interatrial septum where the sheath includes a side port proximal to the positioning balloons, and the additional catheter or wire advances through the side port, and capturing the wire member with the additional catheter or wire forming a loop with the captured wire member.

BRIEF DESCRIPTION OF THE DRAWINGS

The preferred embodiments described herein and illustrated by the drawings hereinafter be to illustrate and not to limit the invention, where like designations denote like elements.

FIG. 1A is a side perspective, cross-sectional view of an embodiment of a transseptal insertion device.

FIG. 1B is a side perspective, cross-sectional view of an embodiment of a transseptal insertion device showing a dilator extending partially through and extending out from device.

FIGS. 19A-19C are a side view, a close side view, and a cross-sectional end view of a puncture tip of an embodiment of an improved transseptal puncture system with puncture member balloon seal with a deflated puncture member balloon.

FIGS. 20A-20C are a side view, a close side view, and a cross-sectional end view of a puncture tip of an embodiment of an improved transseptal puncture system with puncture member balloon seal with an inflated puncture member balloon.

FIGS. 21A-21B are cross-sectional side view and a close, cross-sectional side view of a puncture tip of an embodiment of an improved transseptal puncture system with puncture member balloon seal with an inflated positioning balloon.

FIGS. 22A-22B are cross-sectional side view and a close, cross-sectional side view of a puncture tip of an embodiment of an improved transseptal puncture system with puncture member balloon seal with a deflated positioning balloon.

FIGS. 23A-23C show an embodiment of an improved transseptal puncture member balloon that is inflated through the inflation port once the puncture member is outside the shaft and is tenting the septum, guidewire that is advanced into the left atrium, and the puncture member balloon that is deflated.

FIGS. 25A-25C show side views of the distal end portion of the puncture member multi-lumen extension, and a cross-sectional view of the distal end portion of the puncture member multi-lumen extension of the transseptal puncture system.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1C:
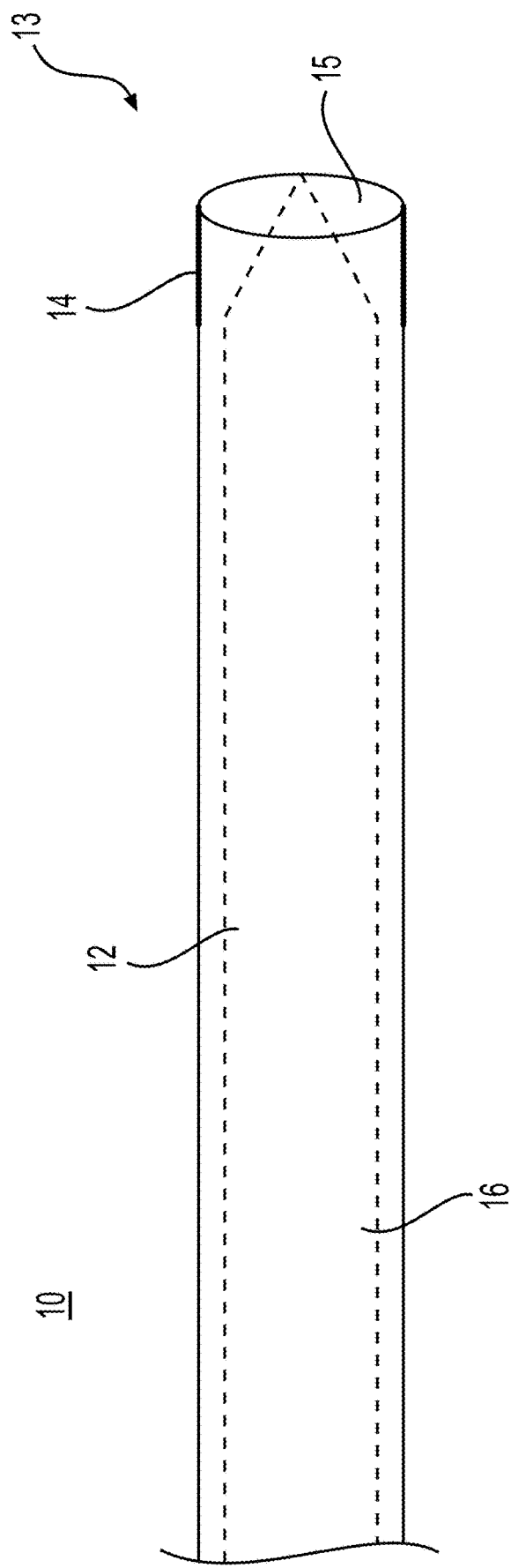
FIG. 1C is a side perspective, cross-sectional view of an embodiment of a transseptal insertion device showing a dilator extending partially through the device.

With reference to FIGS. 1A-1C, shown is an embodiment of transseptal insertion device or catheter 10. Shown is the distal end of transseptal insertion device 10, i.e., the end of transseptal insertion device 10 with opening through which dilator, catheter, and needle may extend, e.g., to puncture interatrial cardiac septum. As shown in FIG. 1A, transseptal insertion device 10 includes outer sheath or balloon shaft 12 and one or more balloons 14 located at distal tip 13 of transseptal insertion device 10. Sheath 12 may contain and define a center lumen 15. Sheath 12 may be fabricated from various materials, including, e.g., polymers, including thermoplastics elastomers (TPEs) such as PEBA (e.g., Pebax®), nylons, thermoplastic polyurethanes (TPUs) such as Pellathane®, similar materials and combinations thereof. Sheath 12 may be referred to as catheter shaft and used in cardiac catheterizations. After puncture, sheath 12 may be inserted through septum into left atrium. Alternatively, sheath 12 may contain a separate catheter that is inserted through septum post puncture. Transseptal insertion device 10 also includes dilator 16, positioned in center lumen 15, as shown in FIG. 1B. The one or more balloons 14 are preferably sealed, air-tight and water-tight, on both its ends to sheath 12.

With continuing reference to FIG. 1A, in view shown, overhanging one or more balloons 14 are uninflated. Although cross-section of balloons 14 shown on top and bottom of distal tip 13, balloons 14 preferably extend around circumference of distal tip or end 13 of transseptal insertion device 10. Overhanging one or more balloons 14 are of form such that balloons 14 overhang or extend from distal tip 13 of sheath 12 when inflated.

In FIG. 1B, dilator 16 is shown positioned within and partially extending out of sheath 12, past distal tip 13 of device 10. Overhanging one or more balloons 14 are uninflated and dilator 16 extends past balloons 14. It is noted that the relative sizes of sheath 12 and dilator 16 shown are for illustrative purposes as the diameter of dilator 16 may be relatively larger or smaller than shown in relation to the diameter of sheath 12, although dilator 16 necessarily has a smaller diameter than sheath 12. Although dilator 16 is shown to have a pointed end, dilator 16 may have a rounded or relatively flat end. Embodiments, as described herein, are designed and intended to puncture septum without use of a needle or other sharp instrument.

With reference now to FIG. 1C, dilator 16 is shown positioned within center lumen 15 of sheath 12. Tip of dilator 16 is positioned within distal tip 13 of transseptal insertion device 10 sub-planar to end of transseptal insertion device 10. The position shown is position dilator 16 may be in immediately prior to inflation of one or more balloons 14. It is noted that the relative sizes of catheter/sheath 12 and dilator 16 shown are for illustrative purposes as the diameter of dilator 16 may be relatively larger or smaller than shown in relation to the diameter of sheath 12. Ordinarily, dilator 16 has smaller diameter or gauge then catheter/sheath 12, although fit of dilator 16 in catheter/sheath 12 is preferably snug enough so that dilator 16 does not move (laterally or axially) relative to position or "wobble" within transseptal insertion device 10. Dilator 16 necessarily has a smaller diameter than sheath 12. In embodiments, sheath 12 material may be sufficiently malleable to enable larger diameter dilators 16, and other larger diameter devices, to be passed through sheath 12. In such embodiments, sheath 12 will stretch to accommodate the larger diameter dilator 16 or other device.

Figure 2A:
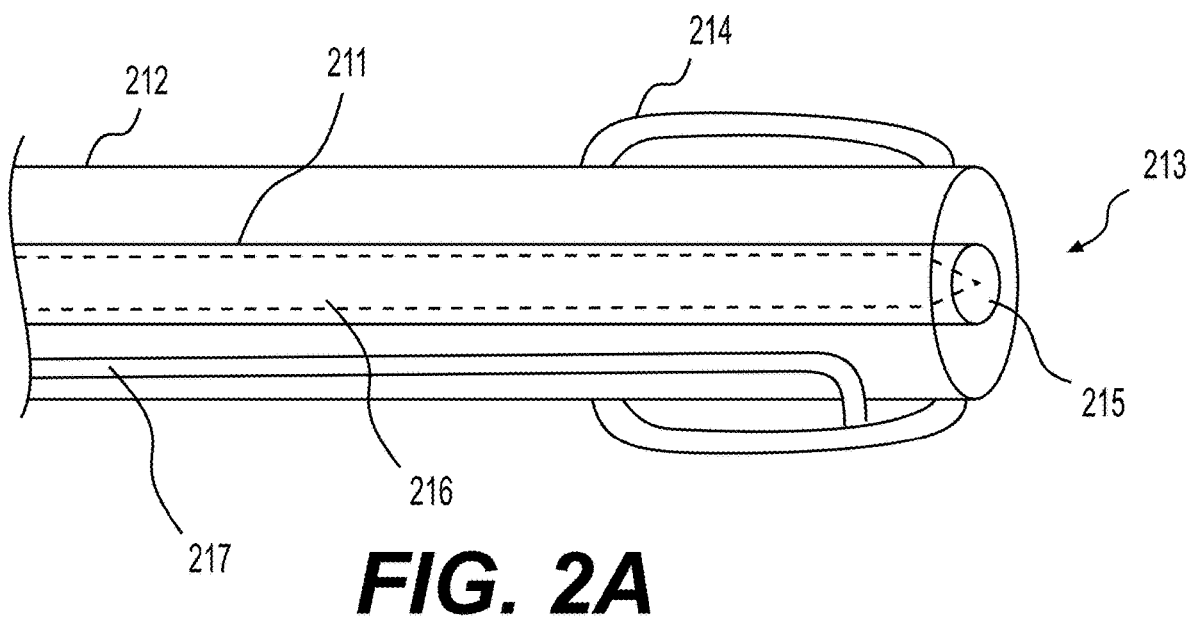
FIG. 2A is a is a perspective view of an embodiment of a transseptal insertion device with hypotube connected to one or more balloons.
Figure 2B:
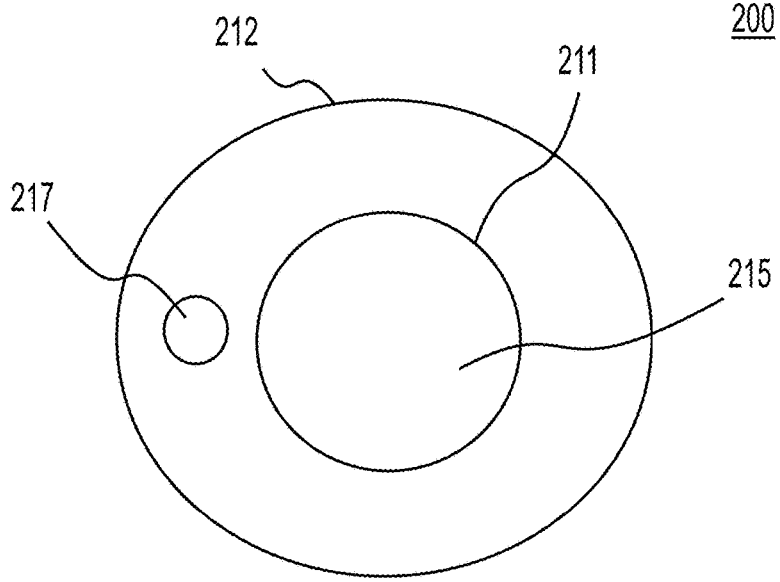
FIG. 2B is a is a front view of an embodiment of a transseptal insertion device with hypotube connected to one or more balloons.

With reference to FIG. 2A, shown is a side perspective view of an embodiment of transseptal insertion device or catheter 200. Shown is the distal end of transseptal insertion device 200, i.e., the end of transseptal insertion device 200 with opening through which dilator, catheter, and needle may extend, e.g., to puncture interatrial cardiac septum. As shown in FIG. 2A, transseptal insertion device 200 includes outer sheath or catheter shaft 212 and one or more balloons 214 located at distal tip 213 of transseptal insertion device 200. Sheath 212 may contain lumen shaft 211 that defines center lumen 215. Sheath 212 may be fabricated from various materials, including, e.g., polymers, including thermoplastics elastomers (TPEs) such as PEBA (e.g., Pebax®), nylons, thermoplastic polyurethanes (TPUs) such as Pellathane®, similar materials and combinations thereof. Sheath 212 may be referred to as catheter shaft and used in cardiac catheterizations. After puncture, sheath 212 may be inserted through septum into left atrium. Alternatively, sheath 212 may contain multiple lumen shafts that define multiple lumens separately. Transseptal insertion device 200 also includes dilator 216, positioned in center lumen 215. The one or more balloons 214 are preferably sealed, air-tight and water-tight, on both their ends to sheath 212. Transseptal insertion device 200 includes hypotube 217 for inflation or deflation of one or more balloons 214. Hypotube 217 may be contained in sheath or catheter shaft 212. Transseptal insertion device 200 may further include a port (not shown) connected to hypotube 217 to supply gas or fluid to inflate one or more balloons 214, or to remove gas or fluid from one or more balloons 214 to deflate balloons 214. Balloons 214 may be fully inflated or deflated, or may be inflated or deflated as much as desired. With reference to FIG. 2B, shown is a front, cross-sectional view of distal end 213 of the embodiment of transseptal insertion device 200 that shows cross-sectional views of sheath 212, center lumen 215, and hypotube 217.

Figure 2C:
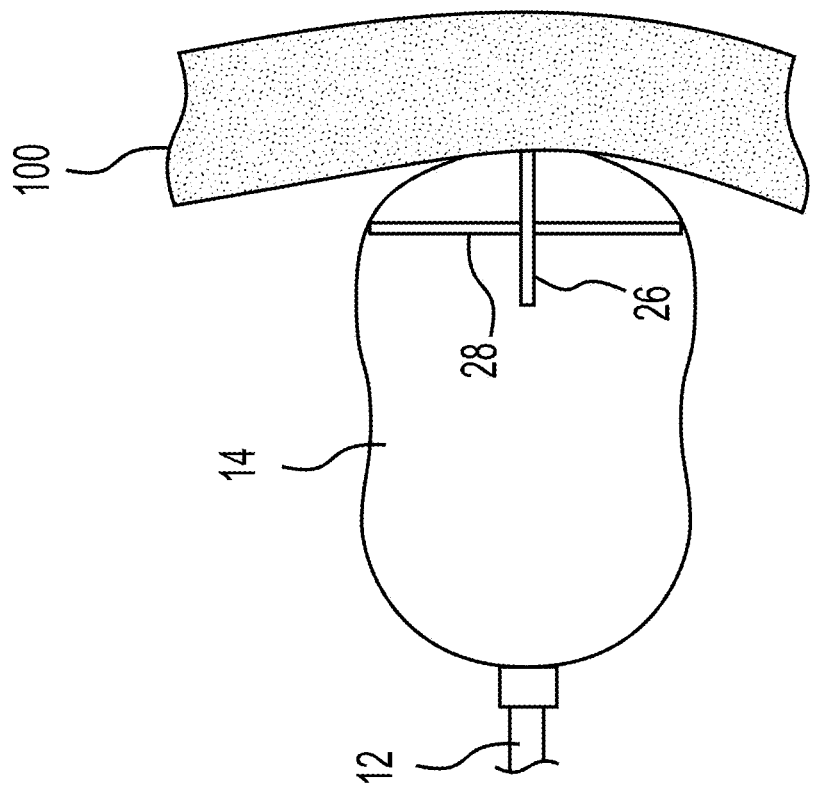
FIGS. 2C-2D are side views of embodiments of transseptal insertion device with ultrasound imaging or visualizing capability.
Figure 2D:
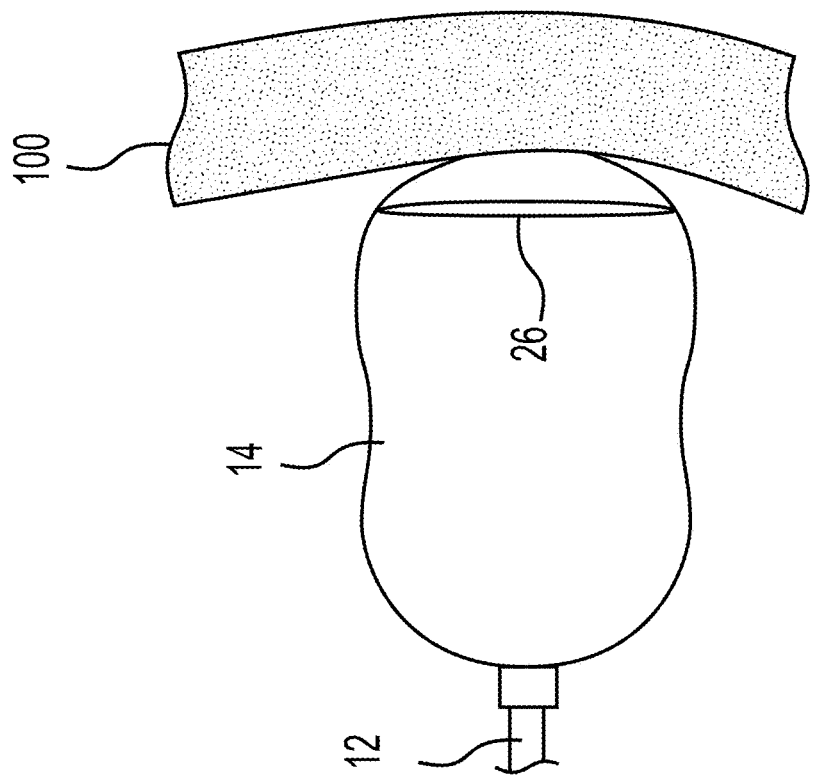

In the embodiment shown in FIGS. 2A-2B, transseptal insertion device 200 may include ultrasound chips or transducers 26 for ultrasound imaging or visualizing (see FIGS. 2C-2D). The transseptal sheath 212 or balloon 214 may house (inside or on) an ultrasound chip or transducer which may be used to guide the insertion procedure. Ultrasound chip or transducer emits and receives ultrasound energy, that may be detected by known ultrasound visualization devices, to create an image of the cardiac chambers (e.g., the right atrium, fossa, interatrial septum, left atrium, atrial appendage, mitral valve, ventricle, etc.). Ultrasound chips and transducers are transducers that convert ultrasound waves to electrical signals and/or vice versa. Those that both transmit and receive may also be called ultrasound transceivers; many ultrasound sensors besides being sensors are indeed transceivers because they can both sense and transmit. Such imaging will allow the operator(s) of transseptal insertion device 200 to visualize the cardiac chambers and the determine the location of the distal end or tip 213 of transseptal insertion device 200, enabling more precise operation of transseptal insertion device 200. Such ultrasound chips or transducers used may be similar to ultrasound chip or transducer described in US Pat. App. Pub. 2003/019546, which is herein incorporated by reference, or any other ultrasound transducer known to those of ordinary skill in the art that may be fabricated on scale small enough to be deployed on or in sheath 212 or balloon 214.

With reference to FIGS. 2C-2D, shown are embodiments of transseptal insertion device 200 with ultrasound imaging or visualizing capability. Balloon 14 shown includes one or more ultrasound chips or transducers 26 deployed in or on balloon 14. Ultrasound chips or transducers 26 may be ultrasound transceivers that both emit and receive waves, convert the ultrasound waves to electrical signals, transmit the electrical signals, e.g., through a wire that runs via sheath 12. Ultrasound chips or transducers 26 may be connected via WiFi or other wireless connection, to an external imaging device that produces images from the received signals (both still and video images).

Ultrasound chips or transducers 26 may be affixed to interior or exterior surface of balloon 14. Ultrasound chips or transducers 26 may be arranged in a line, disc, or cross-shape. Ultrasound chips or transducers 26 may be arranged to be forward facing (e.g., on distal end of balloon facing towards interatrial septum), as shown in FIG. 2C, or in a different direction/orientation, such as sideways and forward facing (e.g., facing towards interatrial septum and facing perpendicular to the distal or front end), as shown in FIG. 2D. Indeed, orientation of ultrasound chips or transducers 26 may depend on whether balloon 14 is inflated or not. When balloon 14 is fully inflated, as shown in FIG. 2C, ultrasound transducer 26 may be forward facing (or forward and perpendicularly facing as shown in FIG. 2D). However, when balloon 14 is deflated, ultrasound transducer 26 may be folded flat and positioned on side of distal tip 13 of sheath 12. Hence, when balloon 14 is deflated, ultrasound chip or transducer 26 may be side-facing. During inflation ultrasound transducer 26 orientation will change as balloon 14 inflates (moving from side-facing orientation to forward facing orientation with the ultrasound transducer 26 shown in FIG. 2C). Accordingly, operator(s) of transseptal insertion device 200 may vary the inflation of balloon 14 to achieve different orientations of ultrasound transducer 26 for different imaging views.

Ultrasound chip or transducers 26 may emit and/or receive/detect ultrasound waves that may be reflect off of surfaces and structures, e.g., within atrium, and then read by imaging system (not shown), e.g., connected to ultrasound chips or transducers 26 via wire or cable extending through, e.g., lumen 15 in sheath 12. In this manner, ultrasound chips or transducers 26 may enable visualization of the interatrial septum and the left atrial structures.

It is also noted that ultrasound chips or transducers 26 may be deployed on distal tip 13 of sheath 12 (or elsewhere on or in sheath 12). Ultrasound chips or transducers 26 may be installed or configured to be forward facing (facing towards distal end of sheath 12). Alternatively, ultrasound chips or transducers 26 may be flipped to be rear facing (facing towards proximal end of sheath 12). Varying orientations of ultrasound chips or transducers 26 may be implemented.

Figure 3A:
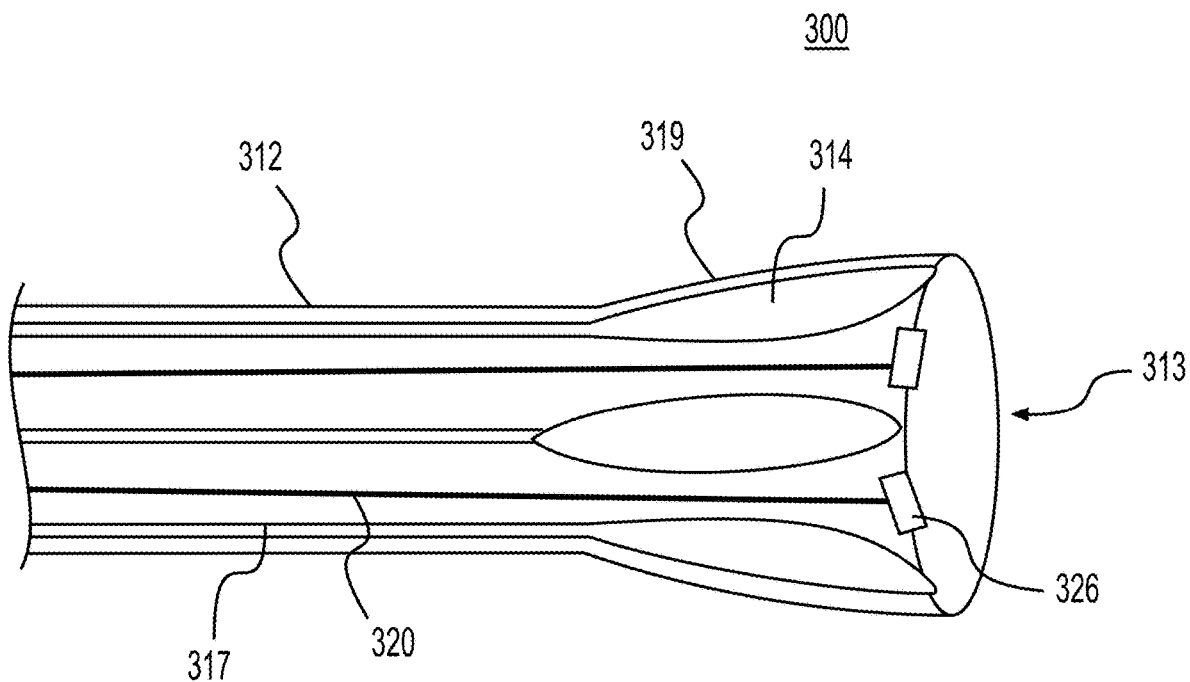
FIG. 3A is a is a perspective view of an embodiment of a transseptal insertion device with multiple balloons and hypotubes connected to the multiple balloons.
Figure 3B:
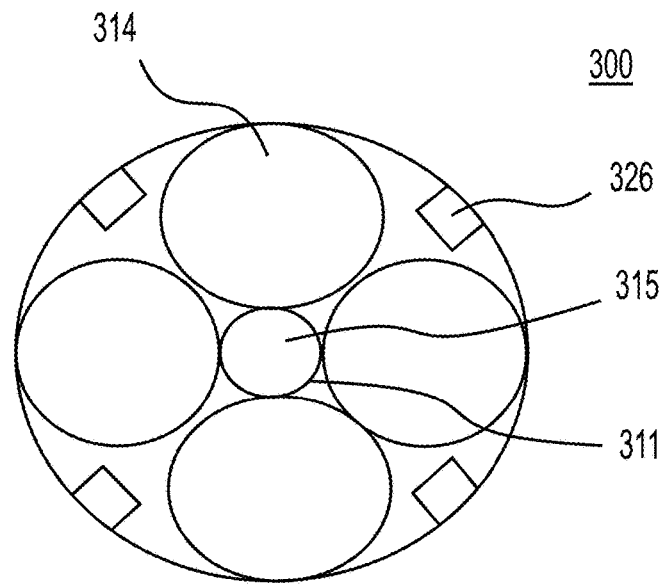
FIG. 3B is a is a front view of an embodiment of a transseptal insertion device with multiple balloons and hypotubes connected to the multiple balloons.

With reference to FIGS. 3A-3B, shown is transseptal insertion device 300 including multiple balloons 314, which surround center lumen shaft 311 that defines center lumen 315, and sheath or catheter shaft 312 that includes center lumen shaft 311 and hypotubes 317 connected to multiple balloons 314. FIG. 3A is a side view of sheath or catheter shaft 312, and FIG. 3B is a front cross-sectional view of sheath or catheter shaft 312. Balloons 314 are in various shapes such as round, cylindrical, spherical, tear drop shaped or pear shaped, and are in various lengths. Balloons 314 may be with or without overhang over shaft. Balloons 314 are positioned around distal tip or end 313, and may extend around circumference of distal tip or end 313. Multiple balloons 314 are connected to one or more hypotubes 317, and inflated or deflated via hypotubes 317 that are contained in sheath or catheter shaft 312. Each of balloons 314 may be connected to corresponding hypotube 317 to independently control the inflation and deflation of balloons 314. Alternatively, balloons 314 may share one or more hypotubes 317. Inflation fluid or gas may flow through hypotubes 314 to inflate or deflate balloons 314. Outer covering 319 may cover the multiple balloons 314.

In between balloons 314, there are one or more ultrasound chips or transducers 326 that provide ultrasound imaging or visualizing capability. For illustrative purposes, FIG. 3B shows ultrasound chips or transducers 326 disposed between balloons 314, but ultrasound chips or transducers 326 may be deployed in or on balloons 314. Ultrasound chips or transducers 326 may be affixed to interior or exterior surface of balloon 314. Ultrasounds chips or transducers 326 may be ultrasound transceivers that both emit and receive waves, convert the ultrasound waves to electrical signals, transmit the electrical signals, e.g., through wire 320 that runs inside sheath or catheter shaft 312. However, ultrasound chips or transducers 326 may be connected wirelessly via WiFi or other wireless connection, to an external imaging device that produces images from the received signals (both still and video images).

Ultrasound chips or transducers 326 may be designed in the shape of the balloons 314. The balloons 314 may be round, cylindrical, spherical, tear drop shaped or pear shaped with overhang or without overhang. Ultrasound chips or transducers 326 may have shapes corresponding to the shapes of balloons 314. Alternatively, one or more ultrasound chips or transducers 326 may be deployed in a shape corresponding to the shapes of balloons 314. Depending on the shapes of balloons 314, ultrasound chips or transducers 326 may be side facing, front facing or back facing. Ultrasound chips or transducers 326 may be arranged in a line, disc, or cross-shape. Ultrasound chips or transducers 326 may be arranged to be forward facing (e.g., on distal end of balloon facing towards interatrial septum), or in a different direction/orientation, such as sideways and forward facing (e.g., facing towards interatrial septum and facing perpendicular to the distal or front end).

Orientations of ultrasound chips or transducers 326 may depend on whether balloons 314 are inflated or not. When balloons 314 are fully inflated, ultrasound chips or transducers 326 may be forward facing. However, when balloons 314 are deflated, ultrasound chips or transducer 326 may be folded flat and positioned on side of distal tip 313 of center lumen 315. Hence, when balloons 314 are deflated, ultrasound chips or transducer 326 may be side-facing. During inflation, orientation of ultrasound chips or transducers 326 may change as balloons 314 inflate (moving from side-facing orientation to forward facing orientation). Accordingly, operator(s) of transseptal insertion device 300 may vary the inflation of balloons 314 to achieve different orientations of ultrasound chips or transducers 326 for different imaging views.

Figure 4:
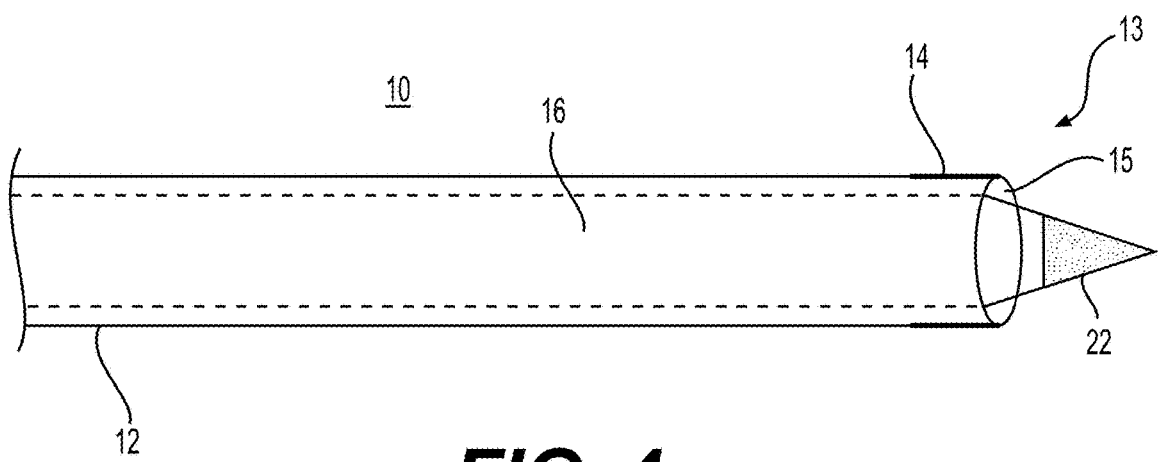
FIG. 4 is a perspective, cross-sectional view of an embodiment of a transseptal insertion device with radiofrequency energy capability.

With reference now to FIG. 4, shown is an embodiment of transseptal insertion device 10 with radiofrequency (RF) energy capability. Transseptal insertion device 10 shown includes sheath 12, overhanging one or more balloons 14, and dilator 16. Dilator 16 may include cap or crown 22, on distal end as shown, with RF energy capability or capable of delivering RF energy. Alternatively, cap or crown may include or be an RF electrode. Dilator 16 may be connected, e.g., on proximate end (not shown) to a radiofrequency energy source (not shown) at, e.g., external hub, that provides RF energy to cap or crown 22. The RF energy may be delivered through dilator 16. So equipped with cap or crown 22, dilator 16 may tent interaxial septum and create puncture of interaxial septum through delivery of RF energy. In this embodiment, the use of a sharp needle may be avoided. The dilator with cap or crown on distal end with RF energy capability or capable of delivering RF energy may be used for transseptal insertion devices 200 and 300 shown in FIGS. 2A-2B and 3A-3B.

Figure 5:
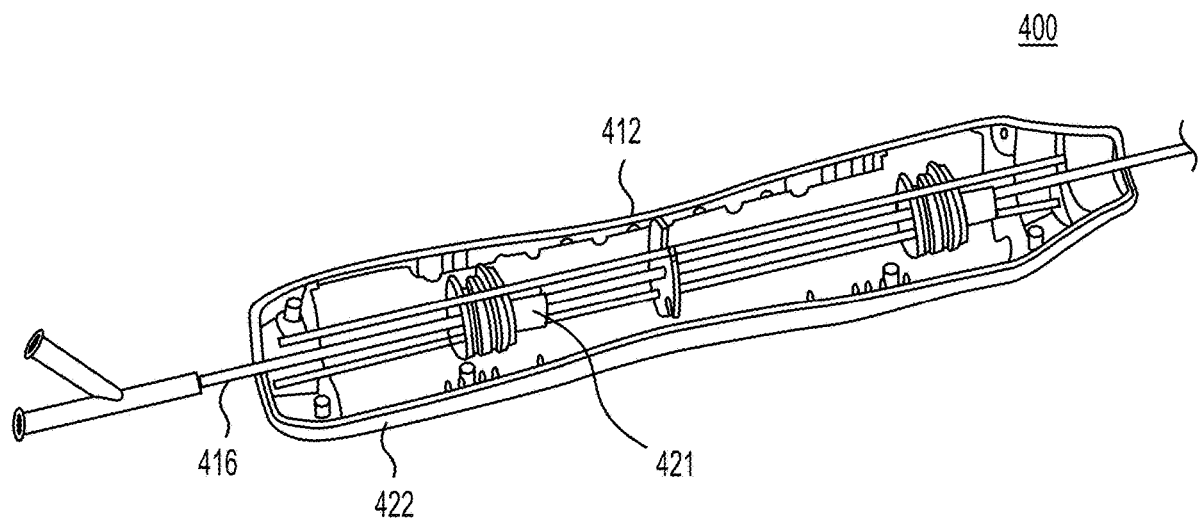
FIG. 5 is a is a perspective view of an embodiment of a transseptal insertion device with a drive assembly coupled to dilator, and knob coupled to the drive assembly.

With reference to FIG. 5, shown is transseptal insertion device 400 including drive assembly 421, which is coupled to dilator 416, and knob 422 coupled to drive assembly 421 to cause dilator 416 to traverse along an axial direction of sheath or catheter shaft 412. Dilator 416 may move backwards or forwards along the axial direction of sheath 412 while knob 422 is rotated. The drive assembly 421 may include nut assembly to drive the dilator 416. Dilator 416 may be with or without RF energy capability.

Figure 6:
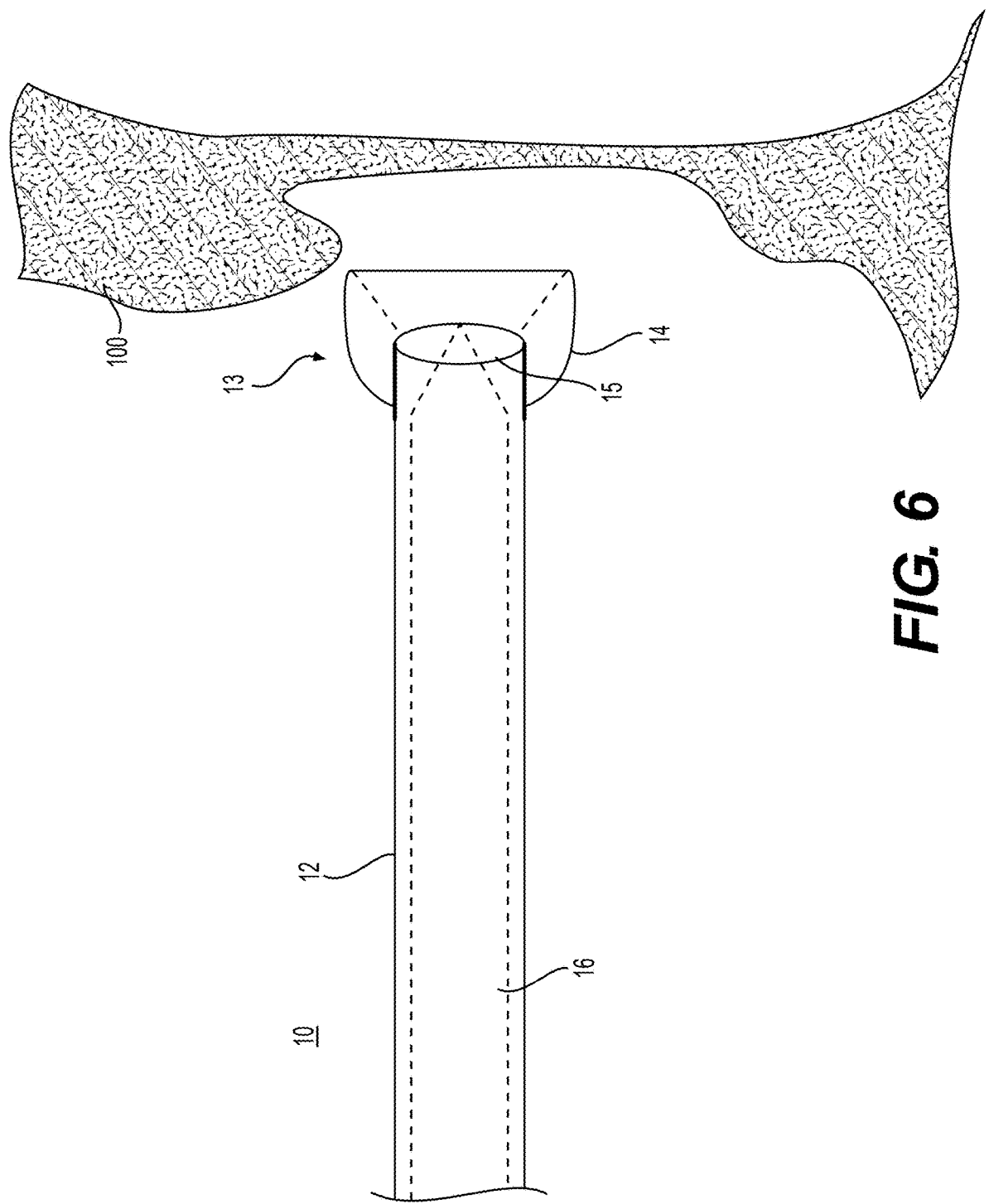
FIG. 6 is a perspective, cross-sectional view of an embodiment of a transseptal insertion device showing inflated overhanging balloon and dilator positioned within device and subplanar to overhanging balloon.

With reference now to FIG. 6, shown is distal end of an embodiment of transseptal insertion device 10 in which overhanging balloons 14 is inflated by supplying gas or fluid into balloon 14 through hypotube (not shown). Dilator 16 is shown positioned within center lumen 15 of sheath 12 with tip of dilator 16 positioned at distal tip 13 of transseptal insertion device 10 and sub-planar to overhanging balloon 14. The plane that is referred to here is the plane perpendicular to the axis of transseptal insertion device 10 and dilator 16, formed by the end of overhanging balloon 14. Hence, dilator 16 remains sub-planar to overhanging balloon 14 until operator intends balloon 14 to be deflated and dilator 16 to tent and puncture interatrial septum 100. As noted above, balloon 14 preferably extends completely around circumference of tip 13 of transseptal insertion device 10. Accordingly, FIG. 7 only illustrates cross-section of inflated balloon 14.

Figure 7:
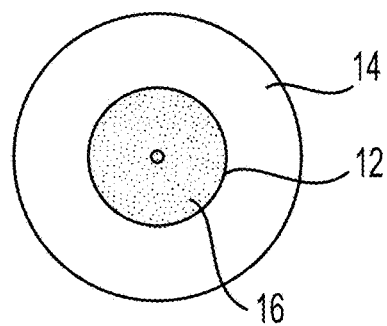
FIG. 7 is a cross-sectional, end view of an embodiment of a transseptal insertion device and dilator shown prior to puncturing an interatrial cardiac septum with inflated overhanging balloon.

With reference now to FIG. 7, shown is a front, cross-sectional view of distal end an embodiment of transseptal insertion device 10 in which overhanging balloon 14 is inflated. As shown, inflated overhanging balloon 14 preferably extends around entire circumference of sheath 12 (and, therefore, device 10). Shown situated within lumen 15 of sheath 12 is tip of dilator 16. Tip of dilator 16 is positioned within tip 13 of transseptal insertion device 10, as it would be prior to being extended past tip 13 and puncturing an interatrial cardiac septum.

Figure 8:
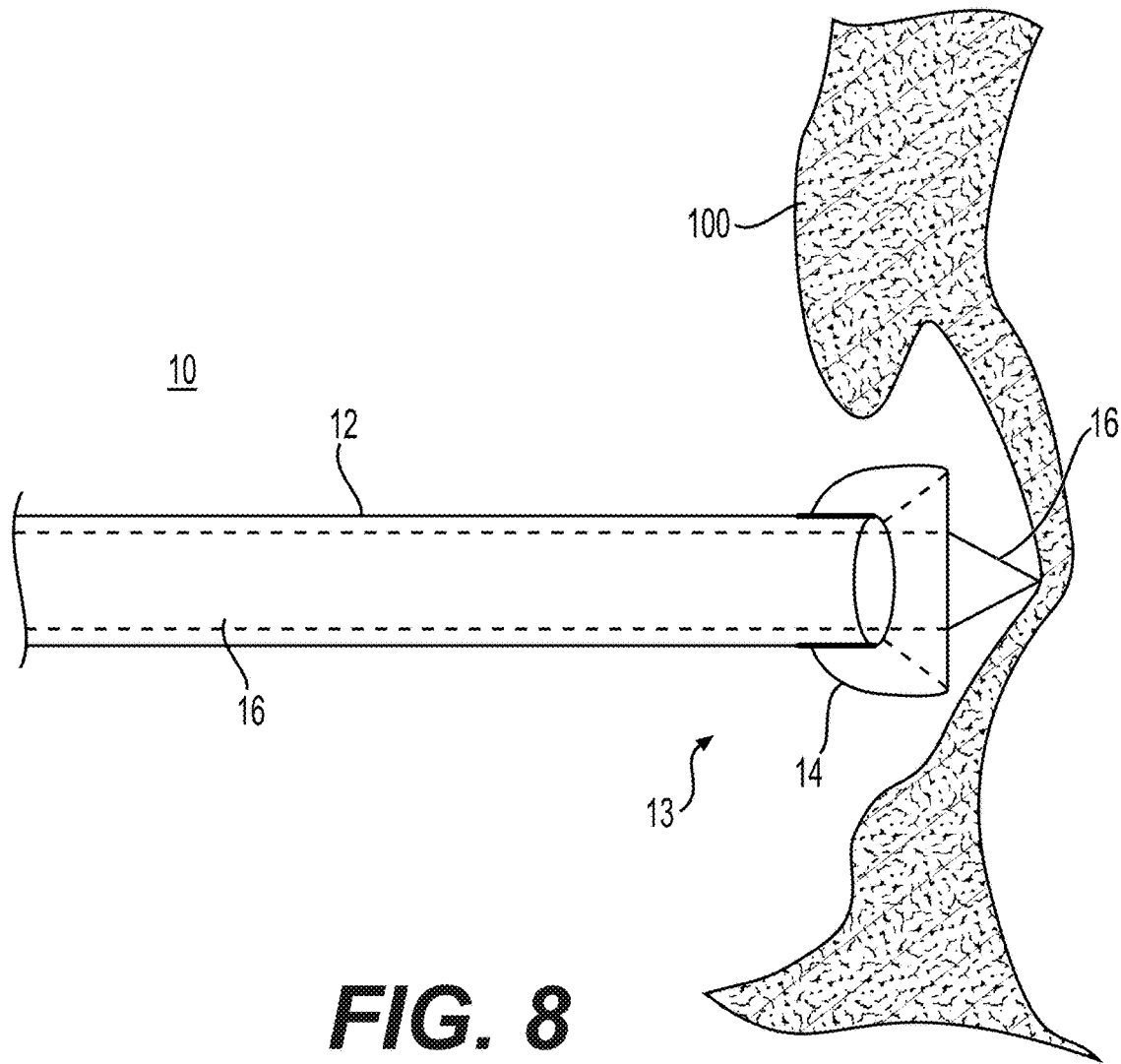
FIG. 8 is a perspective, cross-sectional view of an embodiment of a transseptal insertion device with dilator advanced forward in order to tent an interatrial septum.

With reference now to FIG. 8, shown is distal end of an embodiment of transseptal insertion device 10 with dilator 16 advanced forward in order to tent the interatrial septum 100. Dilator 16 is shown extending through center lumen 15 of sheath 12 and past overhanging balloon 14. At this stage, balloon 14 may be deflated by removing gas or fluid in balloon 14 through hypotube. Extended as such, and pressed against interatrial septum 100, dilator 16 tents the interatrial septum 100 away from transseptal insertion device 10.

Figure 9:
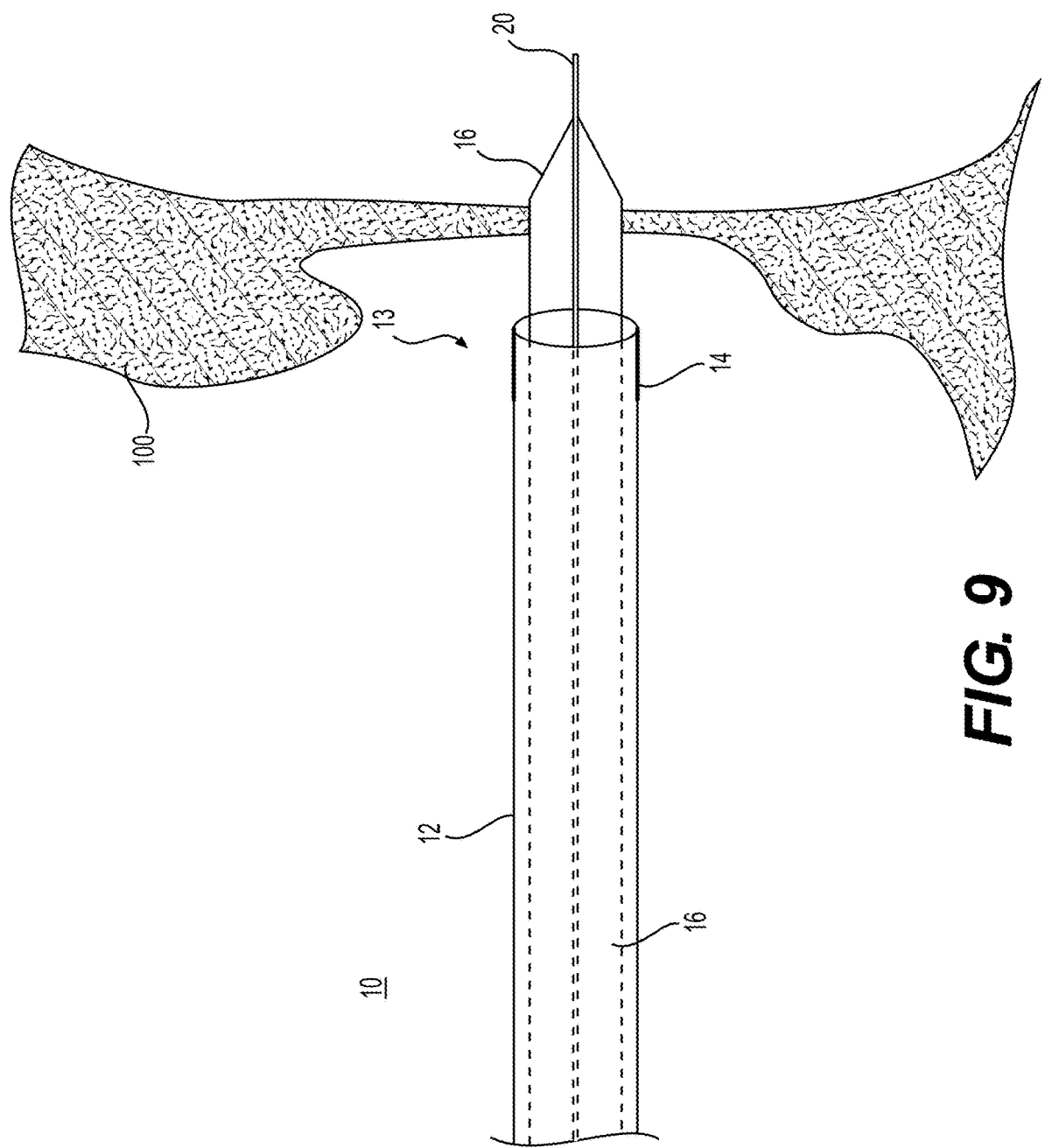
FIG. 9 is a perspective, cross-sectional view of an embodiment of a transseptal insertion device with a transseptal wire advanced post-puncture through interatrial septum.

With reference now to FIG. 9, shown is shown is distal end of an embodiment of transseptal insertion device 10 with dilator 16 advanced forward through interatrial septum 100, after puncturing septal wall (e.g., through application of energy through dilator 16 as described herein) and transseptal wire or wire rail 20 extending through dilator 16 and into left atrium chamber 110. Wire rail 20 may sit in a lumen 19 of dilator 16. Dilator 16 may be used as a conduit to advance the wire rail 20 into the left atrium.

Wire rail 20 may act as a guide for devices to enter the left atrium through the puncture in the septal wall made by transseptal insertion device 10. For example, wire rail 20 may guide transseptal insertion device 10 or other catheters in the left atrium. In this manner, catheters may be advanced safely into the left atrium over or guided by wire rail 20. In an embodiment, wire rail 20 may be energized (e.g., to ablate or puncture the septum with energy delivered from source at proximal end of transseptal insertion device 10).

With continued reference to FIG. 9, dilator 16 preferably defines and includes an opening or lumen 19 extending through its tip and through which transseptal wire 20 extends. With dilator 16 extended as shown and tenting interatrial septum, septum may be punctured by energy delivered through cap or electrode at tip of dilator 16 and transseptal wire rail 20 extended through opening in tip of dilator 16 and through puncture made in interatrial septum by dilator 16 cap.

Figure 10C:
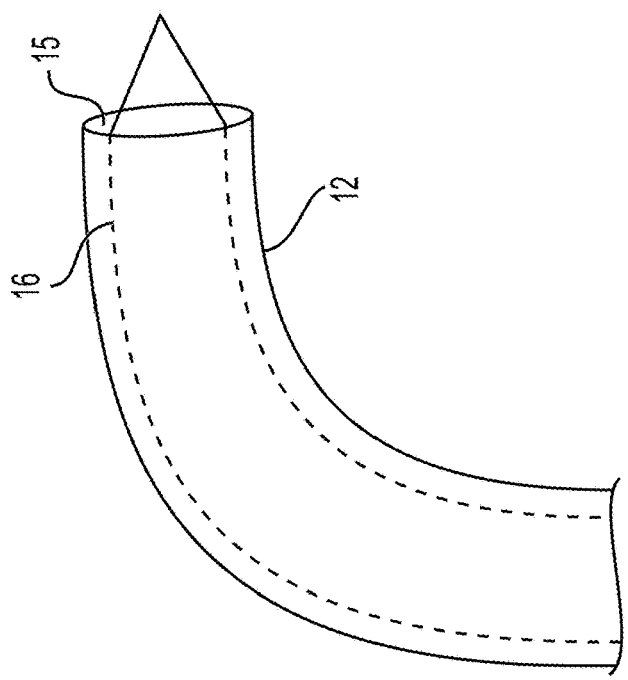
FIGS. 10A-10C are perspective, cross-sectional views of an embodiment of a flexible transseptal insertion device with different angulations.
Figure 10B:
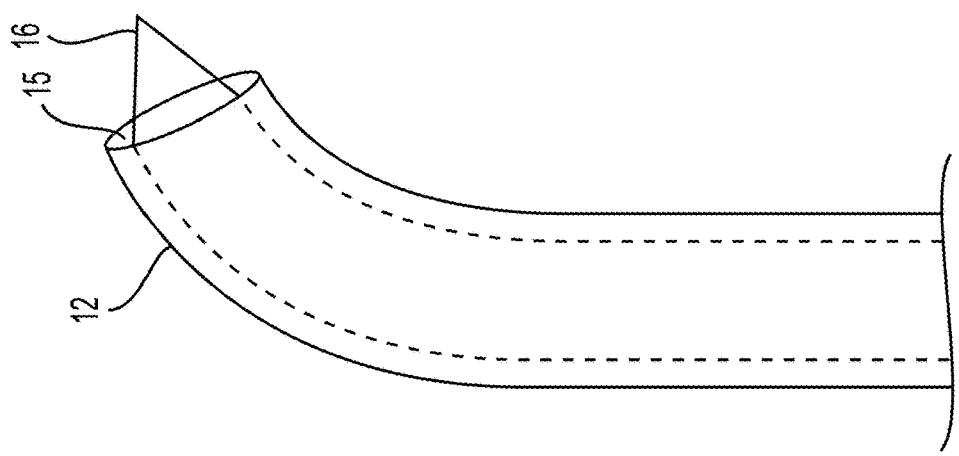
Figure 10A:
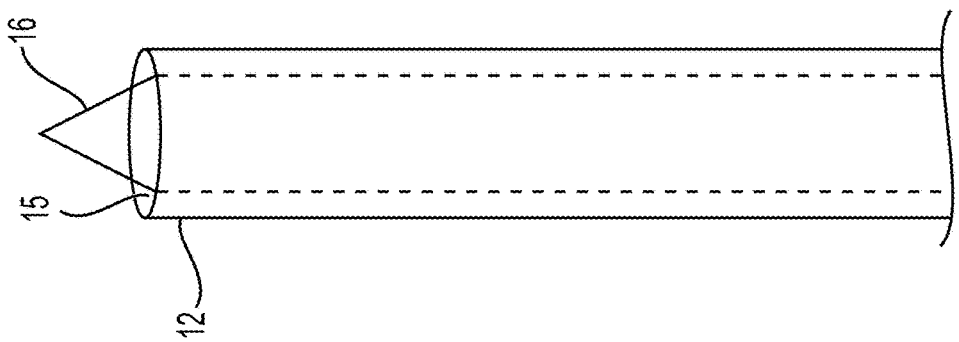

With reference to FIGS. 10A-10C, shown are different views of an embodiment of transseptal insertion device 10 with a flexible sheath 12 flexed or angulated at different angles. Transseptal insertion device 10 may be flexed or angulated depending on the anatomy of the atria using fixed angled dilators 16 that are inserted into lumen shaft of sheath 12, causing sheath 12 to flex. Such fixed angled dilators 16 may be, e.g., any angle from 0-270°. Alternatively, sheath 12, lumen shaft and dilator 16 may be all flexible (preferably, hypotubes, needle and catheter inserted through such flexible sheath 12 are flexible or malleable, at least in part) and transseptal insertion device 10 may be flexed or angulated, thereby flexing or angulating sheath 12 and dilator 16, using, e.g., a handle or wire (not shown) connected to tip 13 of device 10. Handle and/or wire may also be used to turn or flex or move tip 13 of transseptal insertion device 10, e.g., moving tip 13 of sheath "up" or "down" or "left" or "right" or angulating tip 13 relative to axis of sheath 12 as shown.

Figure 11:
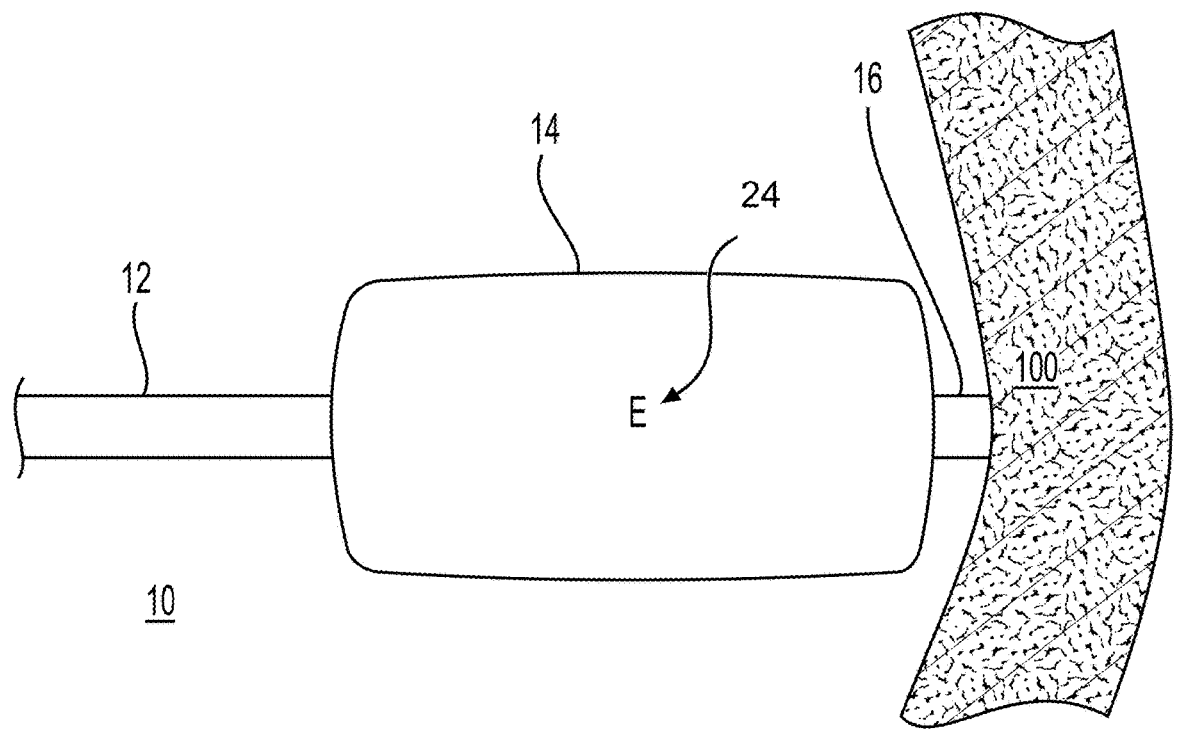
FIG. 11 is a side view of an embodiment of transseptal insertion device with an overhanging balloon with marking.

With reference now to FIG. 11, shown is distal end of an embodiment of transseptal insertion device 10 with inflated overhanging balloon 14. Balloon 14 shown is an embodiment with one or more markers 24. Marker 24 may be, e.g., a radiopaque and/or echogenic marker 24. As a radiopaque or echogenic marker, marker 24 will be visible on scanners used by those performing cardiac catheterizations. The markers 24 may be in the form of letters, such as an E or a C. Marker 24 enables the appropriate positioning of balloon 14 and sheath 12 in the 3-dimensional space (e.g., of the atrium) using imaging to view the marker 24 and, therefore, the position of balloon 14.

Specifically, in operation, the less posterior distal tip 13 is positioned, the more of the E (or C) will be shown. As operator of transseptal insertion device 10 turns or rotates distal tip 13 toward posterior of patient, less of the arms of the E will be seen. In a preferred embodiment, when only the vertical portion of the E is visible (i.e., appearing as an I) distal tip 13 will be rotated to its maximum posterior position.

With continuing reference to FIG. 11, balloon 14 is shown as inflated. However, distal end of dilator 16 is shown extruding or extending distally from balloon 14, past plane formed by distal end of inflated balloon 14. Accordingly, dilator 16 has been moved into the tenting and puncturing position, adjacent to interaxial septum. At this stage, balloon 14 may be deflated or will soon be deflated, and puncture of the interaxial septum is imminent.

Figure 12:
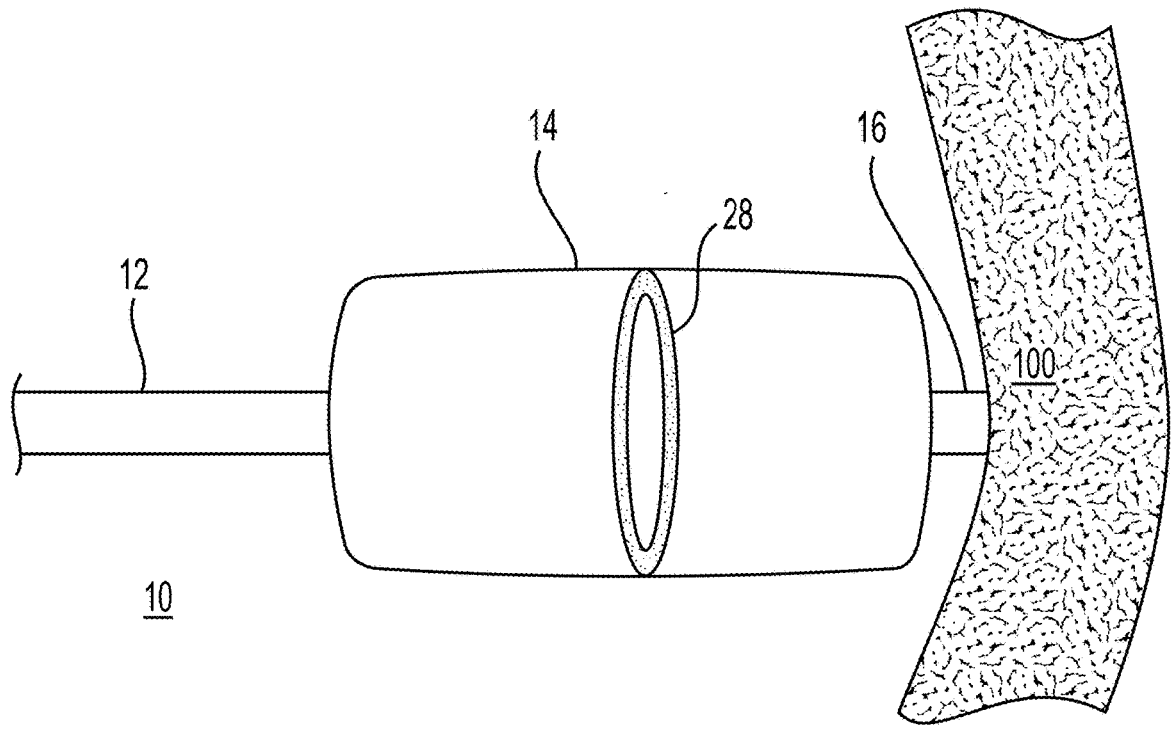
FIG. 12 is a side view of an embodiment of transseptal insertion device with an overhanging balloon with a marker band.

With reference now to FIG. 12, shown is another embodiment of overhanging balloon 14 which may be deployed in embodiments of transseptal insertion device 10. Overhanging balloon 14 may include ring or band 28 around a portion of balloon 14. Ring or band 28 may serve as a marker, similar to markers 24 shown in FIG. 11. Hence, ring 28 may be radiopaque or echogenic and may be view by scanning devices used for visualization in cardiac catheterizations (e.g., fluoroscopic imaging devices). Similar to the letter E or C, the view of the ring 28 changes as the distal tip 13 of transseptal insertion device 10 moves more posterior. When in a least posterior position, ring 28 may appear as just a line or band positioned across axis of transseptal insertion device 10. When device 10 is rotated so that distal tip 13 is significantly closer to the posterior, ring 28 may appear as a full "flat" circle or ring. In FIG. 12, distal tip 13 is partially rotated so that ring 28 is partially visible.

With reference to both FIGS. 11 and 12, the marker 24 and ring 28 are described and shown as located on balloon 14. In embodiments, marker 24 and/or ring 28 may also be located on sheath 12 and/or dilator 16. So located, marker 24 and/or ring 28 would operate in effectively the same manner as described above (i.e., the arms of the E would disappear as the distal end was moved more to the posterior and the ring would become more visible). Markers 24 and/or rings 28 may be placed on all of balloon 14, sheath 12, and dilator 16, or a combination thereof.

Figure 13:
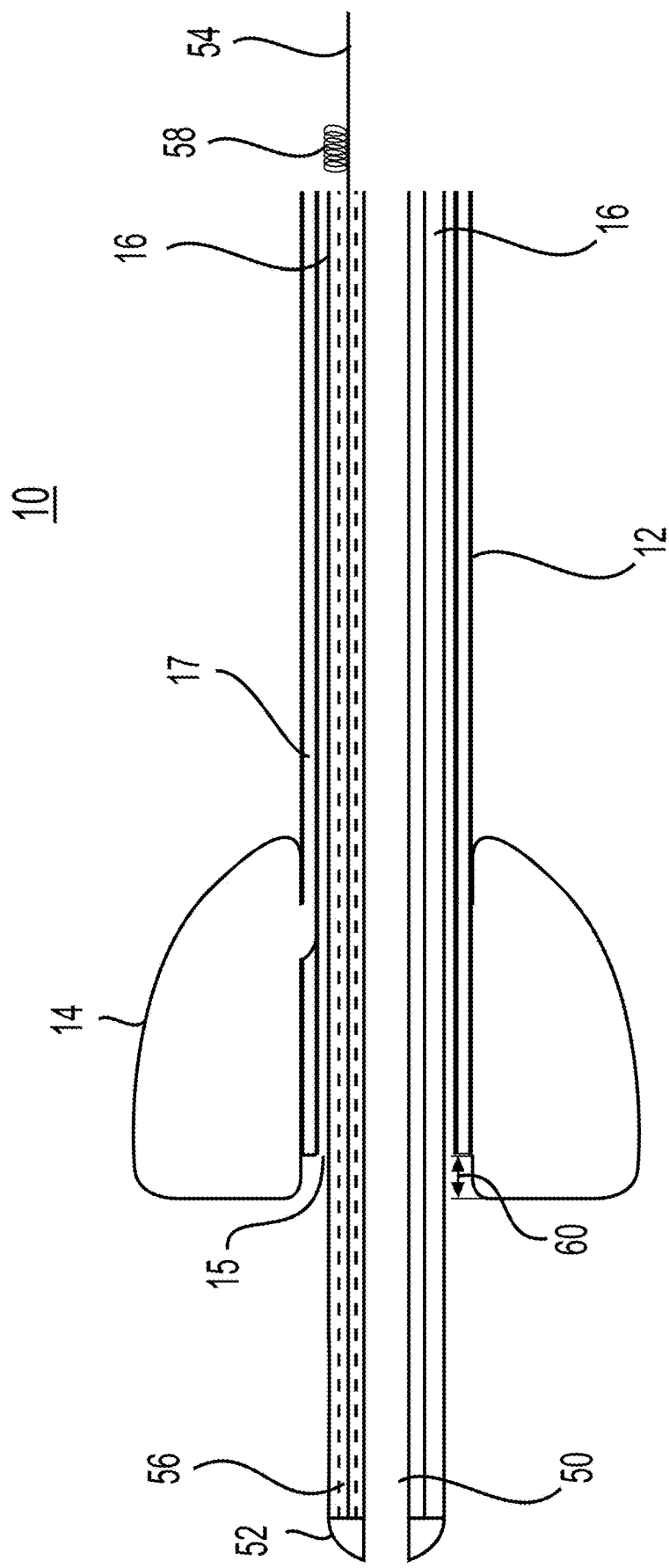
FIG. 13 is a cross-sectional side view of an embodiment of a transseptal insertion device that includes a dilator with an electrode tip.

With reference now to FIG. 13, shown is distal end of an embodiment of transseptal insertion device 10 that includes dilator 16 with electrode tip. Shaft of dilator 16 defines and contains a center lumen 50. Lumen 50 may be defined in the range of, but not limited to, 0.020 to 0.040 inches. Dilator 16 may be made from a polymer material (e.g., HDPE, LDPE, PTFE, or combination thereof). Dilator shaft 16 shown includes a distal electrode tip 52. Electrode tip 52 may comprise a metallic alloy (e.g., PtIr, Au, or combination thereof). In preferred embodiments, the size and shape of electrode tip 52 is selected to be sufficient to generate a plasma for in vivo ablation of tissue in an applied power range of, but not limited to, 20-30W. Electrical conductor 54 extends from electrode tip 52 to the proximal end (not shown) of the dilator 16. Electrical conductor 54 may run axially through an additional lumen 56 defined by and contained in dilator shaft 16. Electrical conductor 54 may contain a coil feature 58 to accommodate lengthening during bending or flexing of dilator 16.

Attached to distal end of sheath 12 is contains overhanging balloon 14 that is connected to hypotube 17. Overhanging balloon 14 may be made from a polymer material (e.g., PET, Nylon, Polyurethane, Polyamide, or combination thereof). Overhanging balloon 14 may be in the range of, but not limited to, 5-20 mm in diameter and 20-30 mm in length. Overhanging balloon 14 may be inflated via injection of gas or fluid through hypotube 17 connected to balloon 14. Overhanging balloon 14 may be deflated by removing gas or fluid in balloon 14 through hypotube 17 connected to balloon 14. During the proper functioning or operation of transseptal insertion device 10 for puncturing the interatrial septum, balloon 14 may be deflated when dilator 16 moves out of lumen 15 by removing gas or fluid from balloon 14. Overhanging balloon 14 is of form such balloon 14 overhangs or extends from distal end 13 of sheath 12. Overhang or extension 60 may be in the range of, but not limited to, 0.0 mm-5.0 mm. The end of the overhang or extension 60 is the plane to which dilator 16 remains sub-planar until moving to tent and puncture the interatrial septum.

Figure 14:
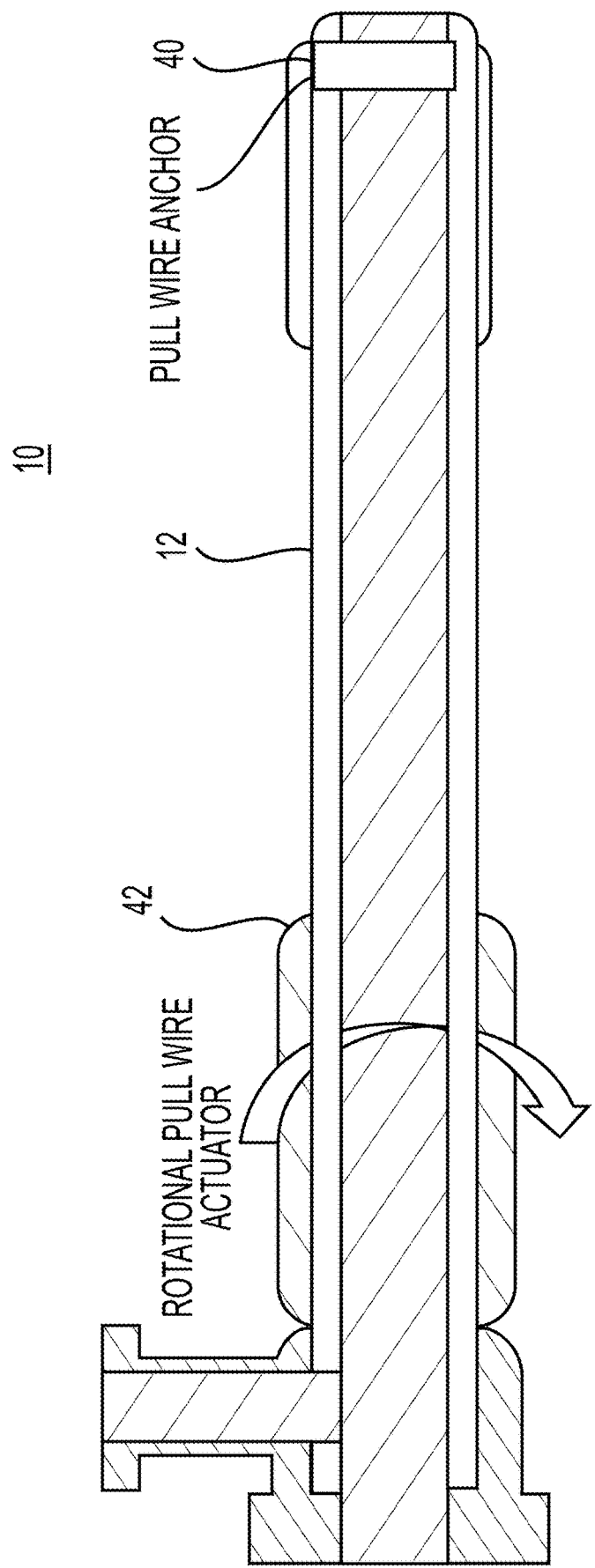
FIG. 14 is a side view of an embodiment of a transseptal insertion device with mechanical deflection capability.

With reference now to FIG. 14, shown is an embodiment of transseptal insertion device 10 that includes a mechanical deflection mechanism. Mechanical deflection mechanism may enable distal end of sheath 12 to be deflected or angulated to various angles with respect to axis of transseptal insertion device 10. Mechanical deflection mechanism may include a pull wire anchor 40 affixed to distal end of sheath 12 and pull wire actuator 42 connected to pull wire anchor 40 with pull wire (not shown). Rotation of pull wire actuator 42, as shown, may exert force on pull wire anchor 40 that deflects or angulates distal end of sheath 12. Pull wire actuator 42 may be rotated by handle connected thereto (not shown). Deflection or angulation of distal end of sheath 12 may enable better intersection (e.g., more perpendicular, flush) with interaxial septum and, therefore, better puncture and insertion by transseptal insertion device 10.

Figure 15:
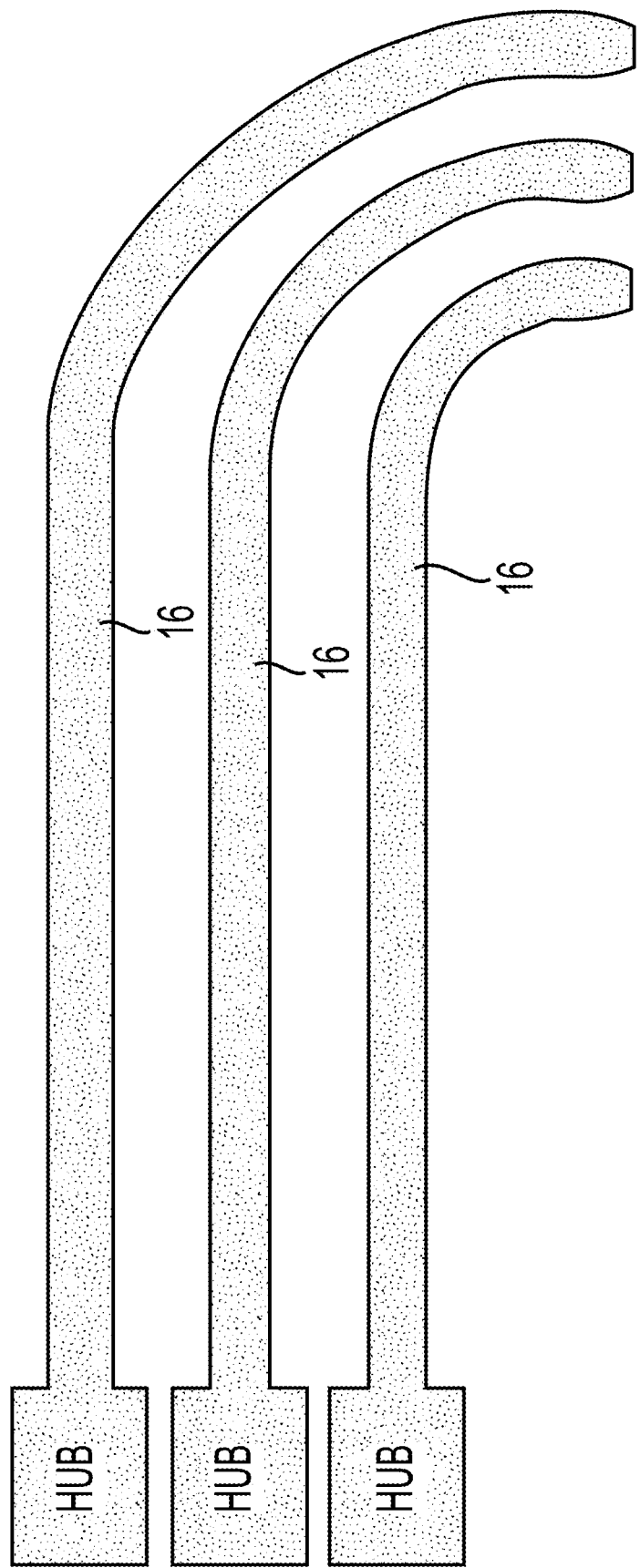
FIG. 15 is side views of embodiments of curved dilators that may be used in embodiments of a transseptal insertion device.

With reference now to FIG. 15, shown are three (3) embodiments of curved dilators 16, each with a different curve profile (i.e., different angle of deflection or curve). Curved dilators 16 may be used in embodiments of transseptal insertion device 10 with flexible or malleable sheath 12. Such a flexible or malleable sheath 12 may be referred to as a steerable sheath 12 as it is "steered" by curved dilator 16 inserted in sheath 12.

Figure 16:
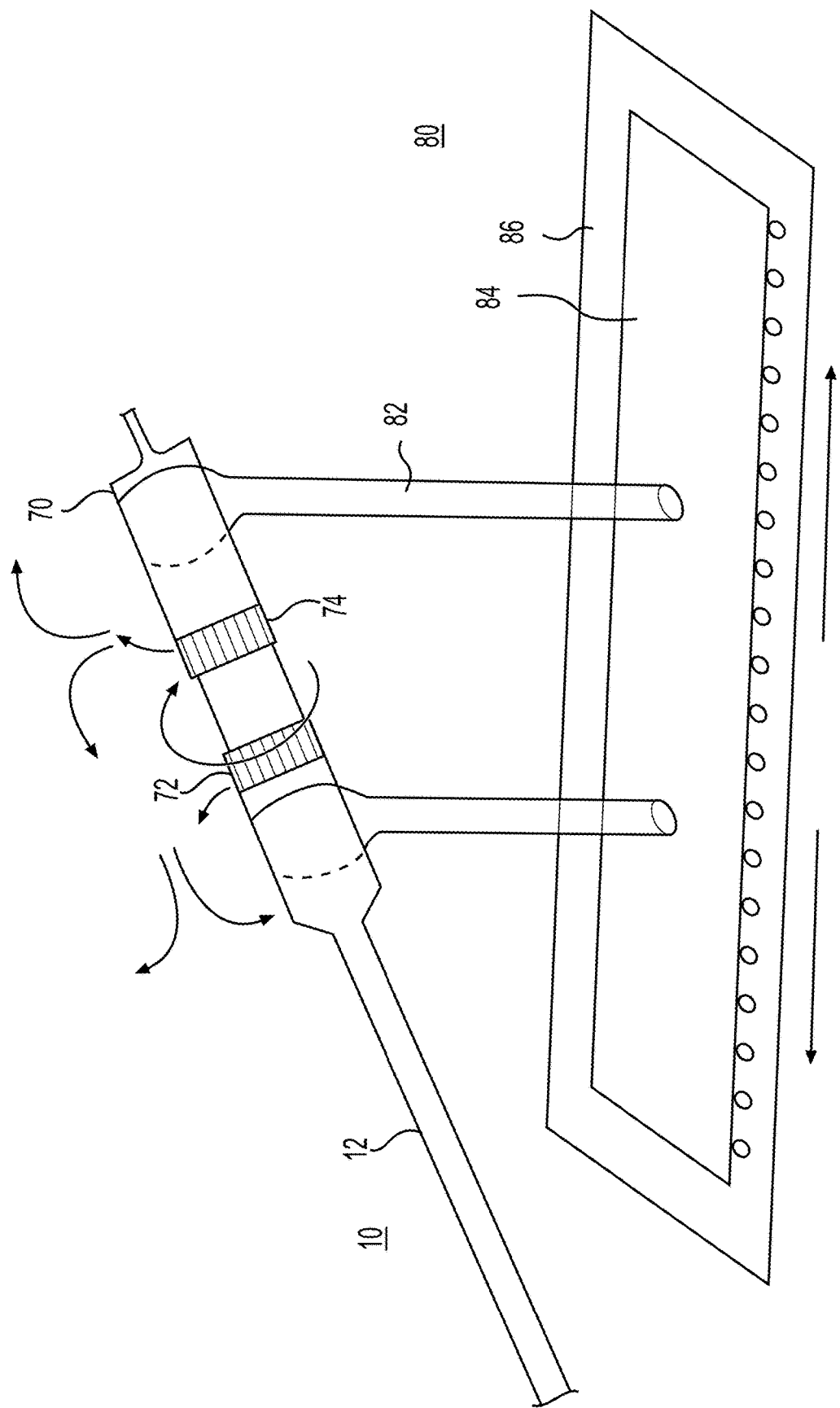
FIG. 16 is a perspective side view of a proximal end of an embodiment of a transseptal insertion device showing a handle and a stabilizer.

With reference now to FIG. 16, shown is an embodiment of transseptal insertion device 10 with an external stabilizer 80. Stabilizer 80 keeps proximal end of transseptal insertion device 10 stable while allowing movement of transseptal insertion device 10 towards the distal and proximal ends of device 10, rotational/torqueing movement of proximal end of device 10, and manipulation of dials or other controls of device 10. In effect, stabilizer 80 substantially prevents unwanted movement of the transseptal insertion device 10 and, importantly, distal end of sheath 12, balloon 14, and dilator 16.

Stabilizer 80 includes connecting rods or arms 82 that connect stabilizer 80 to handle 70 at proximal end of transseptal insertion device 10. Connecting arms 82 are attached to stabilizer platform 84. Connecting arms 82 preferably hold the handle 70 securely and tightly, while permitting desired rotational movements and control manipulation. Stabilizer platform 84 is moveably attached to stabilizer base 86 so that stabilizer platform 84, and hence handle 70 and transseptal insertion device 10, may be slid forwards and backwards along axis of transseptal insertion device 10 towards and away from insertion point in patient (typically femoral vein at the groin of patient). Stabilizer base 86 is typically secured to a flat, stable surface, such as a table, or the leg of the patient. Configured as such, stabilizer 80 prevents unwanted vertical, rotational, or other movement of transseptal insertion device 10 and its handle 70, keeping transseptal insertion device 10 and its handle 70 stable while permitting precise manipulation of handle 70 and its controls.

With continuing reference to FIG. 16, as shown, proximal end of transseptal insertion device 10 may include a handle 70 for control and manipulation of transseptal insertion device 10 and, particularly, dilator 16 and distal end of dilator 16. Handle 70 may include a dial 72 that may be used to turn or deflect distal end of dilator 16, effectively moving the distal end of dilator 16 up or down in relation to axis of transseptal insertion device 10 (as indicated by arrows in FIG. 16). Handle 70 may also include dial 74 for extruding/extending distal end of dilator 16 out of sheath 12 and retracting dilator 16 back into sheath 12, effectively moving dilator 16 along axis of transseptal insertion device 10 (as indicated by arrows in FIG. 16). Handle 70 may also be rotated, as indicated by rotational arrow in FIG. 16, in order to deflect or turn distal end of transseptal insertion device to left or right in relation to axis of transseptal insertion device 10, increasing or decreasing dilator 16 angle of deflection in that direction. If dial 72 moves distal end of dilator 16 along Y axis, and transseptal insertion device 10 axis is considered the Z axis, so that dial 74 moves dilator 16 along Z axis rotating handle 70 moves distal end of transseptal insertion device 10 (and hence distal end of dilator 16) along X axis. Handle 70 includes a port through which dilator 16 and other devices inserted into transseptal insertion device 10 may be inserted. Handle 70 may also include one or more tubes or other ports permitting connection to external hubs and external energy sources, inflation liquids or gas.

In embodiments shown herein, balloon 14 and dilator 16 may be used as energy sources in the left atrium and may be used to deliver energy to the pulmonary veins, left atrial appendage, mitral valve and the left ventricle present in the left atrium. Such embodiments may include external energy sources connected to balloon 14 and/or dilator 16 through wires or other conductors extending lumen in sheath 12. Delivery of energy via balloon 14 or dilator 16 may be thermal/Cryo or radiofrequency, laser or electrical. The delivery of such energy could be through a metallic platform such as a Nitinol cage inside or outside balloon 14. Transseptal insertion device 10 may also include an energy source external to the proximal end of the sheath and operatively connected to balloon 14 to deliver energy to balloon 14.

Figure 17B:
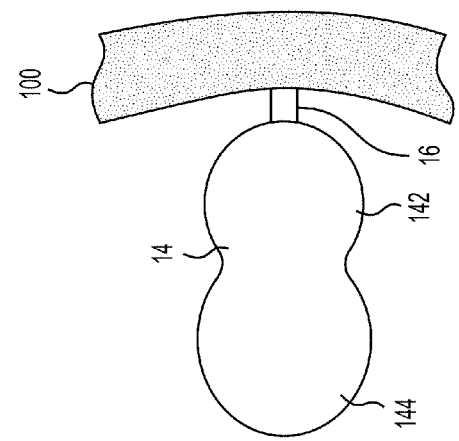
FIGS. 17A-17B are side views of an embodiment of a transseptal insertion device with balloons capable of differential inflation.
Figure 17A:
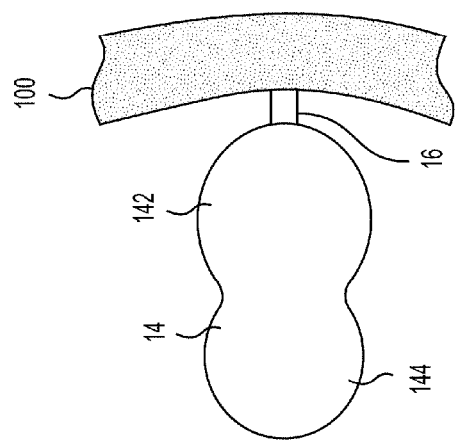

With reference now to FIGS. 17A-17B shown is an embodiment of transseptal insertion device 10 enabling differential expansion of balloon 14. Differential expansion of balloon 14 enables balloon 14 inflation to be adjusted based on the needs of the device operator and the conditions present in the patient's heart. For example, the size of the fossa ovalis portion of the interatrial septum may dictate the desired size of the inflated balloon 14 needed at the puncture site (interatrial septum if often punctured through the fossa ovalis). Fossae can vary greatly in size. The larger the fossa, the harder it will be to tent the interatrial septum with balloon 14. Large fossa tend to be saggy and more difficult to manipulate. Hence, with a large fossa, a larger distal end of balloon 14 will make proper tenting of the interatrial septum easier. Indeed, it may be ideal to have balloon 14 inflated uniformly until intersecting or passing through fossa and then differentially expanding distal end 142 of balloon 14 to move fossa out of the way. In FIG. 17A, distal end or portion 142 of balloon 14 is smaller (less expanded) than proximal end 144 of balloon 14.

Oppositely, the smaller the fossa, the easier it will be to tent the interatrial septum but, there will be less room to maneuver balloon 14 near interatrial septum. Consequently, a smaller distal end of balloon 14 is desired. It also may be beneficial to expand the proximal portion 144 more in order to help fix or secure balloon 14 in place. In FIG. 17B, distal end or portion 142 of balloon 14 is larger (more expanded) than proximal end or portion of balloon 14. In both FIGS. 17A and 17B, dilator 16 has extruded from sheath 12 and past distal end of balloon 14, tenting interatrial septum 100, and puncture is imminent.

This differential expansion of balloon 14 may be achieved, e.g., by using different materials for different portions of balloon 14 (e.g., a more expandable material for distal end 142 than proximal end or portion 144, or vice versa). In general, balloon 14 may be made of either compliant or non-compliant material, or a combination thereof. Compliant material will continue expanding as more inflating liquid or gas is added to balloon 14 (at least until failure). Non-compliant material will only inflate up to a set expansion or designated inflation level. Combinations of compliant and non-compliant material may be used to provide a differentially expanding balloon 14. For example, distal end 142 may be formed from compliant material and proximal end 144 from non-compliant material to enable a larger distal end 142. Oppositely, proximal end 144 may be formed from compliant material and distal end 142 from non-compliant material to enable a larger proximal end 144. Other means for providing differential expansion of balloon 14 may be used, such as applying energy to different portions of balloon 14 to increase or decrease the compliance, and expandability, of that portion.

Balloon 14 may also be used to direct other equipment into these anatomical locations or be used as an angiographic or hemodynamic monitoring balloon. Differential expansion of balloon 14 may be utilized for proper orientation or direction of such equipment.

Figure 18:
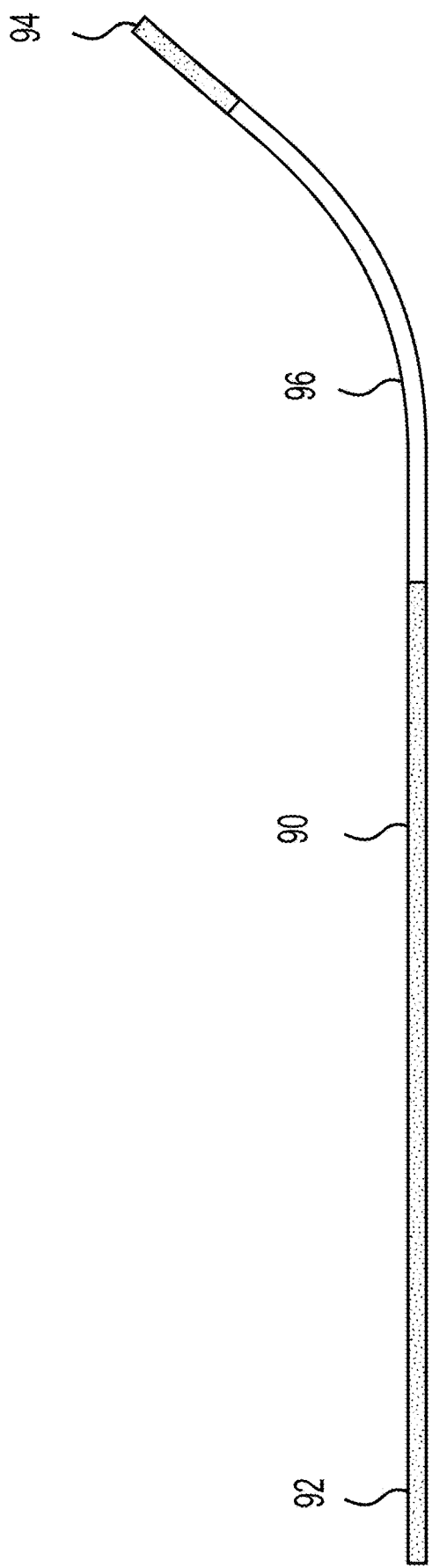
FIG. 18 is a side view of a malleable or flexible transseptal needle that may be used in embodiments of a flexible transseptal insertion device with multiple angulations.

With reference now to FIG. 18, shown is an embodiment of a malleable transseptal needle 90 that may be used with transseptal insertion device 10 with a flexible sheath or otherwise capable of multiple angulations. In embodiments, malleable transseptal needle 90 may be of a variety of diameters and lengths. For example, embodiments include an 18 gauge transseptal needle and that is available in 71 cm, 89 cm, and 98 cm lengths. In embodiments, the malleable transseptal needle has different stiffness in a proximal segment 92, distal segment 94, and in a middle segment 96 between. For example, malleable transseptal needle 90 may be stiffer in the proximal segment 92 and distal segment 94 and more flexible (less stiff) in a middle segment or midsection 96. The mid-section may be the section where transseptal insertion device 10 and dilator 16 angulate. In an embodiment, malleable transseptal needle 90 is used and a control handle provided that enables three-dimensional movements. Malleable transseptal needle 90 shown is, preferably, malleable or flexible at least in part. Proximal end 92 of malleable transseptal needle 90 may be stiff (e.g., made from a stiff material, such as a metal). Mid-section or middle 96 of malleable transseptal needle 90 may be malleable or flexible (e.g., made from a flexible, malleable material, such as rubber). Accordingly, mid-section may flex or bend, enabling malleable transseptal needle 90 to pass through angulated or flexed sheath 12.

Distal end 94 of malleable transseptal needle 90 (i.e., end that punctures interatrial cardiac septum) may be stiff with a cap or electrode at its tip for delivering energy to interatrial septum to puncture interatrial septum. In embodiments, transseptal needle is able to transmit radiofrequency energy to create a controlled septal puncture. Such a transseptal needle may or may not be malleable, but is able deliver RF energy through a cap or crown (e.g., an electrode) at its distal end tip. The needle 90 may be connected, e.g., on proximate end (not shown) to a radiofrequency (RF) energy source (not shown) at, e.g., external hub, that provides RF energy through needle to its distal end tip. In such an embodiment, dilator 16 may tent interaxial septum and RF energy capable transseptal needle may create puncture of interaxial septum through delivery of RF energy.

Embodiments may include an additional dilator which would be able to dilate the distal end of sheath 12, or the entire sheath length, thereby significantly increasing the French size of the sheath 12. For example, balloons deployed within sheath 12 may be inflated to expand sheath 12. In such embodiments, transseptal insertion device 10 may, therefore, be used to accommodate and deliver larger devices or be able to retrieve devices once they have been extruded from sheath 12 and have embolized. Such balloons may be inflated through one or more hypotubes.

In embodiments, energy, typically electrical energy, may directed through transseptal insertion device 10 may be used to increase or decrease the French size of sheath 12. In such embodiments, sheath 12 is fabricated from materials that are known to increase in malleability and or expand when certain energies are applied. In this manner, the French size of sheath 12 may be adjusted to a size deemed necessary during a given procedure. Such energy may be applied through wires or conductive material, connected to energy source external to proximal end of transseptal insertion device 10, attached to or fabricated within sheath 12 or other components of transseptal insertion device 10. Likewise, parts or portions of transseptal insertion device 10 may be selectively made more rigid or more malleable/soft with the application of energy. Therefore, with the application of differential energy to different parts of transseptal insertion device 10 at different times, transseptal insertion device 10 size may be adjusted to enable various devices that are ordinarily larger and bulkier than the catheter to traverse through the catheter. In embodiments, transseptal insertion device 10 may accommodate devices up to 36 Fr.

In an embodiment of transseptal insertion device 10, visualization of an intrathoracic region of interest using MRI techniques may be provided. Embodiments may, for example, provide a needle system comprising a hollow needle having a distal portion and a proximal portion, said distal portion having a distal-most end sharpened for penetrating a myocardial wall. The needle may include a first conductor, an insulator/dielectric applied to cover the first conductor over the proximal portion of said needle and a second conductor applied to cover the insulator/dielectric. The method may further direct the needle system into proximity to a myocardial wall, track progress of the needle system using active MRI tracking, penetrate the myocardial wall to approach the intrathoracic region of interest, and, use the needle system as an MRI antenna to receive magnetic resonance signals from the intrathoracic region of interest.

In related embodiments, MRI antenna may be installed on distal tip 13 of sheath 12, dilator 16 or on balloon 14, similar to ultrasound chips or transducers 226 or 326 described above. Wires connecting such MM antenna or other MRI components may pass through lumen in dilator 16 or sheath 12 and connect with appropriate magnetic resonance energy source on exterior of distal end of transseptal insertion device 10.

With reference now to FIGS. 19A-22B, shown are an embodiment of an improved transseptal puncture system 500 with puncture member balloon seal. With reference to FIGS. 19A-19C, shown are a side view, a close-in side view of the section C, and a cross-sectional view of the section D-D of the transseptal puncture device 500, respectively, when the puncture member balloon 504 is deflated. With reference now to FIGS. 20A-20C, shown are a side view, a close-in side view of the section E, and a cross-sectional view of the section F-F of the transseptal puncture device 500, respectively, when the puncture member balloon 504 is inflated.

Referring to FIGS. 19A-20C, the transseptal puncture device 500 includes a radio-frequency (RF) generator plug 501, Y-connector 502, and puncture member multi-lumen extension 503 that includes sheath 514 and puncture member 515 (see FIG. 21B). The RF generator plug 501 is connected to the puncture member multi-lumen extension 503 through a Y-connector 502, and provides power for a RF generator (not shown) that may be positioned in the puncture member located in the multi-lumen extension 503. The puncture member 515 is located inside the sheath 514, and has a distal end (puncture tip) 506 that is positioned toward the cardiac interatrial septum of the patient when the device 500 is in use. The puncture member balloon 504 is mounted on the puncture member 515 and is located near the distal end 506 of the puncture member 515. The close-in side view FIG. 19B and the cross-sectional view FIG. 19C show deflated puncture member balloon 504, while the close-in side view FIG. 20B and the cross-sectional view FIG. 20C show inflated puncture member balloon 504.

The puncture member 515 includes an puncture member tube 507 for inflating or deflating the puncture member balloon 504, and a lumen 508 which is connected to the puncture member tube 507 that supplies gas or fluid to the puncture member tube 507 to inflate the puncture member balloon 504. The puncture member 515 also includes at least one RF tip 505 at the distal end 506 of the puncture member 515. The RF tip 505 is capable of delivering RF energy. The RF generator (not shown) produces RF energy, and the RF energy is supplied to the RF tip 505. The puncture member 515 includes a lumen 509 for wires that delivers RF energy to the RF tip 505.

With reference to FIGS. 21A-21B, shown are a side view and a close-in side view of the section D of the transseptal puncture device 500, respectively, when the positioning balloon 510 is inflated. The puncture member multi-lumen extension 503 includes the sheath 514 and the puncture member 515. The sheath 514 may have the sheath marker band 513, and the puncture member balloon 504, which is mounted on the puncture member 515, may be aligned with the sheath marker band 513. The sheath 514 includes one or more positioning balloons 510, one or more inflation ports 512 connected to the positioning balloons 510, and at least one tube 516 that delivers gas or fluid to the inflation port 512 to inflate the positioning balloons 510. The tube 516 may be the hypotube 17 (see FIG. 13). The sheath 514 also includes one or more deflation ports 511 that is connected to the positioning balloons 510. When the puncture member balloon 504 is inflated, the inflated puncture member balloon 504 seals the one or more deflation ports 511 in the sheath 514, preventing leak from the positioning balloons 510 and permitting inflation of the positioning balloons 510. The position balloons 510 are then inflated through the inflation port 512 of the sheath 514. The non-compliant or semi-compliant puncture member balloon 504 seals off the deflation ports 511 of the sheath 514, allowing the positioning balloons 510 to inflate and position the distal end 506 of the puncture member 515 to the fossa ovalis (see FIG. 6 for example).

With reference to FIGS. 22A-22B, shown are a side view and a close-in side view of the section B of transseptal puncture device 500, respectively, when the puncture member 515 advances toward fossa ovalis. Once precisely positioned, the puncture member 515 is then pushed distally towards the fossa ovalis. The inflated puncture member balloon 504 moves away from the deflation ports 511, exposing the deflation ports 511. The positioning balloons 510 deflate through the deflation ports 511. However, the positioning balloons 510 may be deflated through both inflation ports 512 and the deflation ports 511.

Figures 24A, 24B:
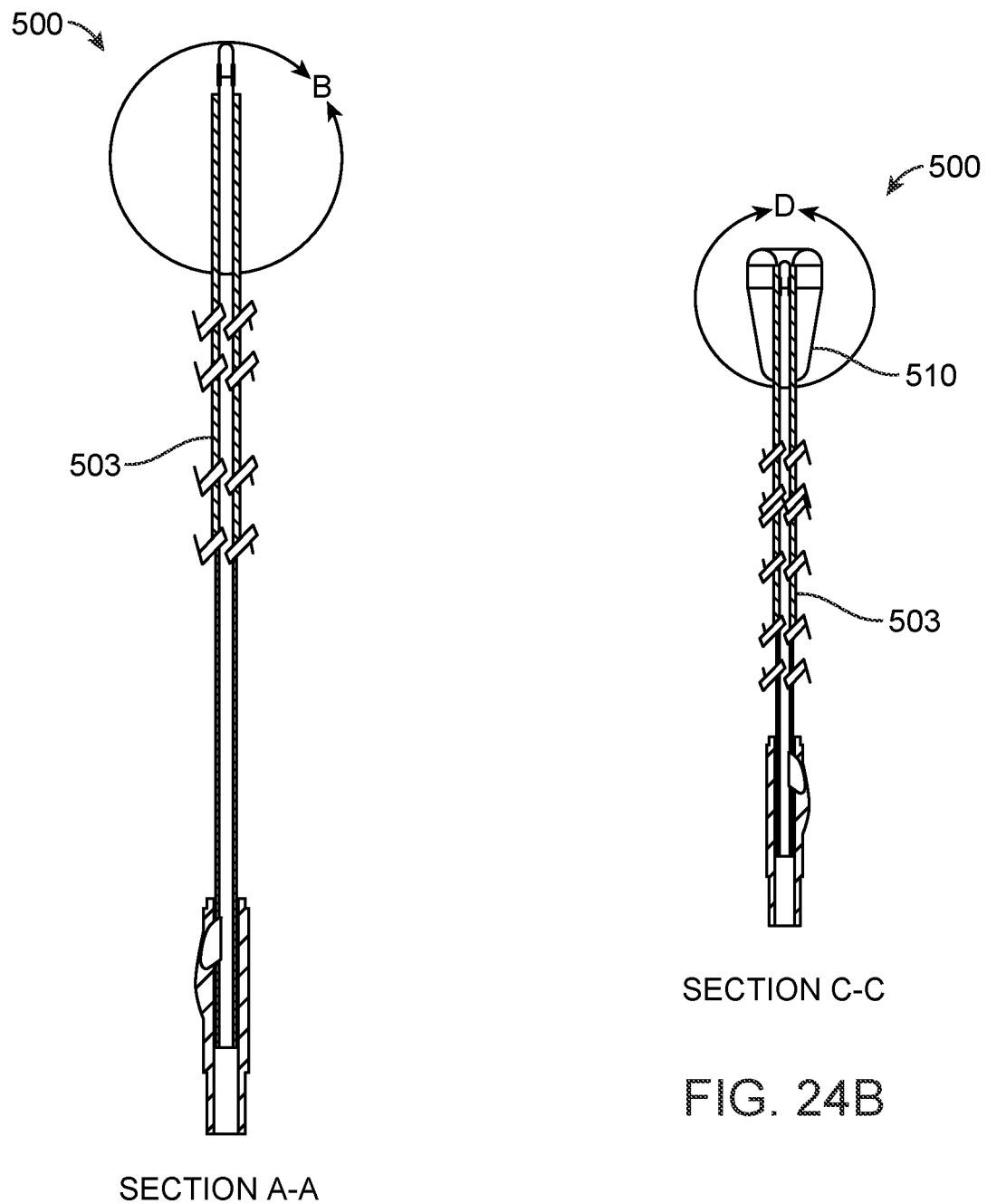
FIGS. 24A-24B show an embodiment of an improved positioning balloon on the shaft that has a separate hypotube for inflation and deflation.

Additional embodiments, implementations, applications and methods of use of the above improved transseptal puncture system are possible. With reference now to FIGS. 23A-23C, shown are a close-in side view of the section E with inflated balloon, a close-in side view of section C with deflated balloon, and a cross-sectional view of the section D-D of the transseptal puncture device 500, respectively. With reference now to FIGS. 24A-24B, shown are a side view of a puncture member that is advanced beyond a shaft and a side view of a puncture member with inflated balloon 510 of the transseptal puncture device 500, respectively. With reference to FIGS. 25A-25C, shown are side views of the distal end portion of the puncture member multi-lumen extension 503 and a cross-sectional view of the distal end portion of the puncture member multi-lumen extension 503 of the transseptal puncture device 500 of the additional embodiment, respectively.

In these embodiments, a method of using the improved transseptal puncture system may use the puncture member balloon 504 for visibility, anchoring against the septum and preventing inadvertent advancement into the left atrium. In such an embodiment, the transseptal puncture member balloon 504 is inflated (see FIG. 23A) through the puncture member tube 507, once the puncture member is outside the shaft and is tenting the septum (i.e., the puncture member balloon is pressing against the septum, tenting the septum away from shaft end). The puncture member balloon 504 is 5 to 8 mm (distance L in FIG. 25B) proximal to the tip of the puncture member and prevents the puncture member from being pushed beyond the 5 to 8 mm into the left atrium. After successful puncture of the interatrial septum, a 035 (0.035") guidewire in the guide wire access lumen (or center lumen) 518 (See FIG. 23C) is advanced into the left atrium and the puncture member balloon 504 is deflated (see FIG. 23B) and the puncture member withdrawn back into the shaft.

In the embodiments, the positioning balloon 510 on the sheath or shaft 514 may have separate hypotubes for inflation and deflation. For example, the sheath 514 may have inflation hypotube 516a and a deflation hypotube 516b to inflate and deflate the positioning balloon 510, respectively. However, the embodiment is not limited to this configuration. The positioning balloons 510 may be inflated and deflated through the same hypotube (for example, see FIG. 3A). The puncture member 515 has a puncture member tube 507 to inflate and deflate the puncture member balloon 504. The puncture member has a radiofrequency tip 505 at a distal end of the puncture member 506. For the small, medium and large curl shafts, the puncture member length is small, medium and large. The curl shaft chosen depends on the size of the atrium. For example, a small curl shaft is used for small atrium. When advanced beyond the shaft 514, the puncture member 515 can only be advanced to a max of 5 to 8 mm coming to a hard stop (see FIG. 24A). In another embodiment, the positioning balloon 510 may be inflated through a separate hypotube, overhangs the shaft by 3 mm, and has variable dimension based on the amount of fluid or air infused or insufflated into the balloon (see FIG. 24B). For small, medium and large curl shafts, the puncture member 515 has a conical tip with no radiofrequency or another energy source. The puncture member may have an 0352 lumen (0.0352") to 040 (0.040") lumen 518. Through this lumen, a wire which may or may not have radiofrequency energy capability may be advanced across the septum. Through this lumen a Brockenbrough needle or a radiofrequency tip needle could be advanced and used to cross the septum. In FIGS. 25A-25B, the wiring member 519 may be the wire, Brockenbrough needle, or a radiofrequency tip needle. The transseptal insertion device 500 includes a sheath 514 that defines at least one lumen 517 therein, one or more positioning balloons 510 that are connected to the distal end 506 of the sheath 514, a puncture member 515 movably positioned within the at least one lumen 517, and a puncture member balloon 504 mounted on the puncture member 515. The puncture member 515 defines a center lumen 518 therein, and a wire member 519, for example, is positioned inside the center lumen 518.

Embodiments may also include a method of performing a septostomy using the improved transseptal puncture system 500. In such a method, once the shaft has crossed the septum, the positioning balloon 510 may be used to perform a septostomy. The positioning balloon 510 could be configured in multiple shapes and forms; for example, the positioning balloon may be shaped in a spherical, conical, reverse conical, teardrop shaped, pear-shaped, double-balloon shape with a double balloon being of varying sizes proximally or distally. Embodiments of the improved transseptal puncture system 500 may include two or more positioning balloons 510 adjacent to one another with separate micro-ports connected to the hypotube for external inflation or deflation.

Embodiments may also include methods using the improved transseptal puncture system 500 for atraumatic navigation in the left atrium. Once the shaft 514 of the improved transseptal puncture system 500 has crossed over into the left atrium, the positioning balloon 510 may be re-inflated for navigation in an atraumatic fashion to different parts of the left atrium including navigating to the left atrial appendage, to the pulmonary veins, to the mitral valve and in the left ventricle.

Embodiments may also include methods of using the improved transseptal puncture system 500 wherein the puncture member balloon 504 is used for anchoring the improved transseptal puncture system 500 against the septum. In the embodiments of the method, once the transseptal puncture system 500 is passed into the left atrium, the puncture member balloon 504 is re-inflated and then the system is pulled back. When pulled back, the puncture member balloon 504 acts as an anchor against the septum.

Embodiments may also include methods of using the improved transseptal puncture system 500 wherein the shaft 514 of the system is used as a delivery guiding catheter to deliver devices. The shaft may be used as a delivery guiding catheter for delivering various devices including left atrial appendage occluder devices.

Figure 26:
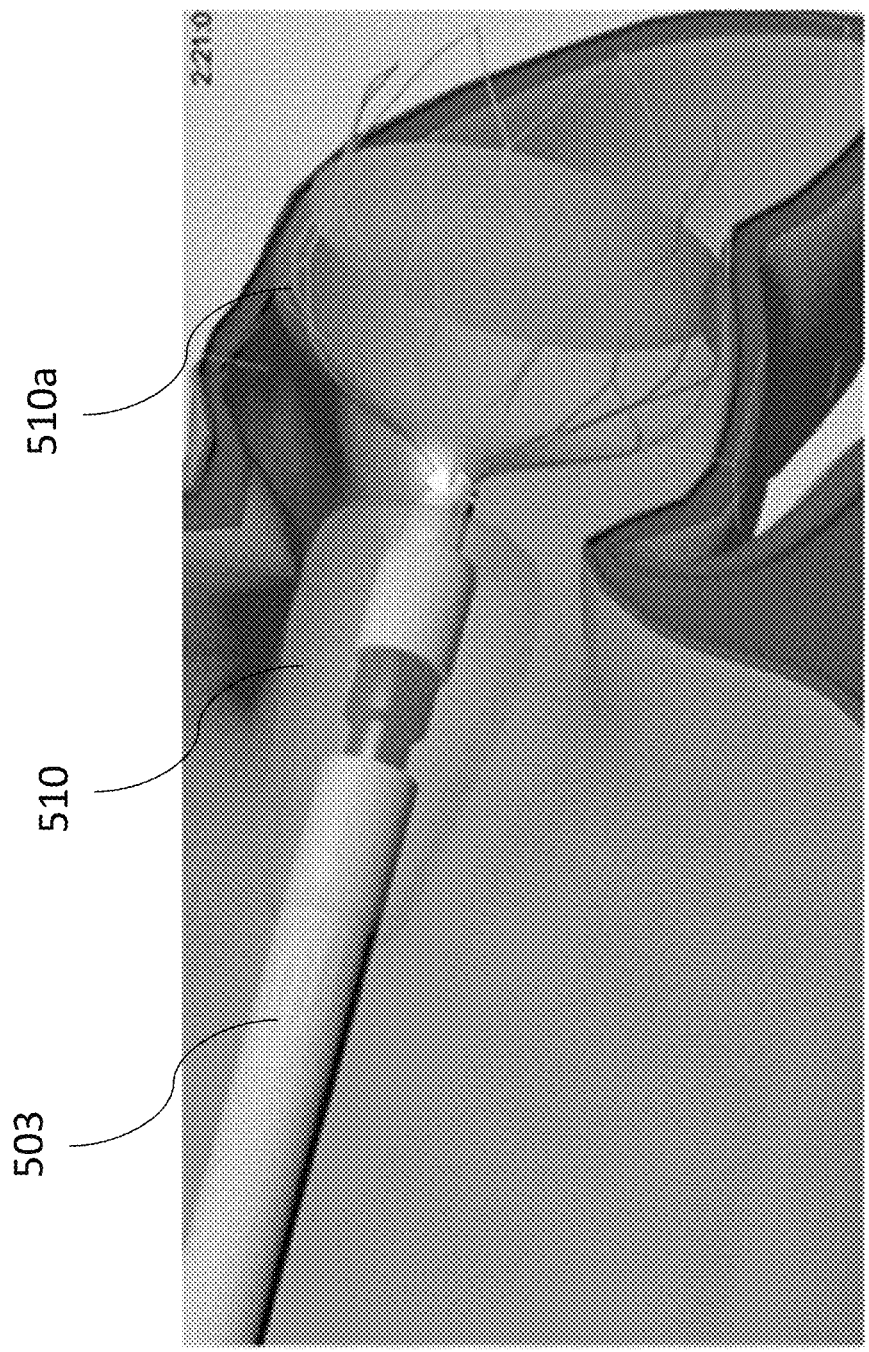
FIG. 26 illustrates an embodiment of a method of using the improved transseptal puncture system.

With reference now to FIG. 26, shown is an embodiment of a method of using the improved transseptal puncture system 500 where the positioning balloon 510a is used as an occlusion balloon. In embodiments, the positioning balloon 510a may be used as an occlusion balloon in the left atrial appendage and pulmonary veins in case of trauma, perforation and bleeding to either the left atrial appendage or pulmonary veins. The catheter 515 may be used in the left atrial appendage with the positioning balloon 510a being inflated such as to occlude the left atrial appendage especially in the eventuality of a perforation. The shaft positioning balloon may be inflated in the left atrial appendage such as to occlude the left atrial appendage.

Figure 27:
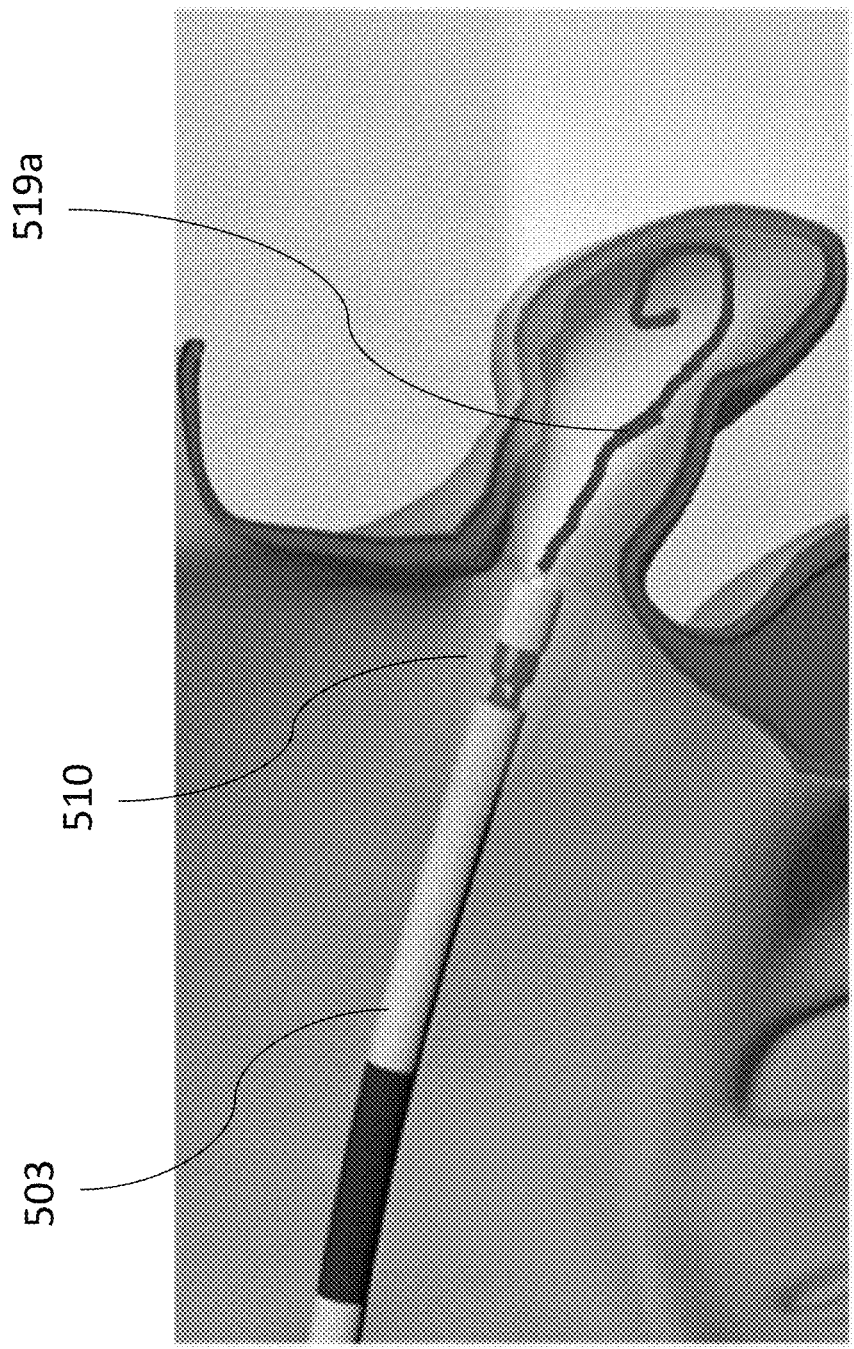
FIG. 27 shows an embodiment of a method of using the improved transseptal puncture system for left atrial appendage thrombectomy.

With reference now to FIG. 27, shown is an embodiment of a method of using the improved transseptal puncture system 500 for left atrial appendage thrombectomy. In the embodiment shown, the improved transseptal puncture system 500 includes a pigtail catheter 519a that is located within the shaft of the guiding catheter. As shown, through the shaft of the guiding catheter a pigtail catheter is advanced into the distal left atrial appendage. Lavage of the left atrial appendage may be performed while injecting fluid, using the pigtail catheter 519a, into the left atrial appendage and aspirating it through the shaft of the guiding catheter. The pigtail catheter 519a may also be used to infuse other pharmaceuticals including thrombolytics in the left atrial appendage.

Embodiments may also include methods using the improved transseptal puncture system 500 for identifying and positioning over a paravalvular leak. The positioning balloon 510 may be used for visualization and anchoring against a prosthetic valves sewing ring annulus and stabilize the guiding catheter such that a paravalvular leak may be traversed with the guiding wire more easily.

Embodiment may also include a method of using the improved transseptal puncture system 500 for laceration of the anterior mitral leaflet. Using the positioning balloon 510, which would be advanced to the anterior mitral leaflet, radiofrequency puncture member 515 or a radiofrequency wire is advanced through the anterior mitral leaflet and advanced into the left ventricle. Embodiments include a side port 509a (see FIG. 25C) in the shaft of the guiding catheter just proximal to the positioning balloon through which a small 4 French Gauge catheter may be passed over a wire into the left ventricle over this catheter or wire. A snare may be passed into the left ventricle. The snare may be used to capture the wire which was placed in the left ventricle through the positioning balloon guide and retracted back into the left atrium. Using this radiofrequency wire which has now formed a loop traversing through the anterior mitral leaflet into the left ventricle and returning back into the left atrium and the anterior mitral leaflet could therefore be lacerated.

Figure 28:
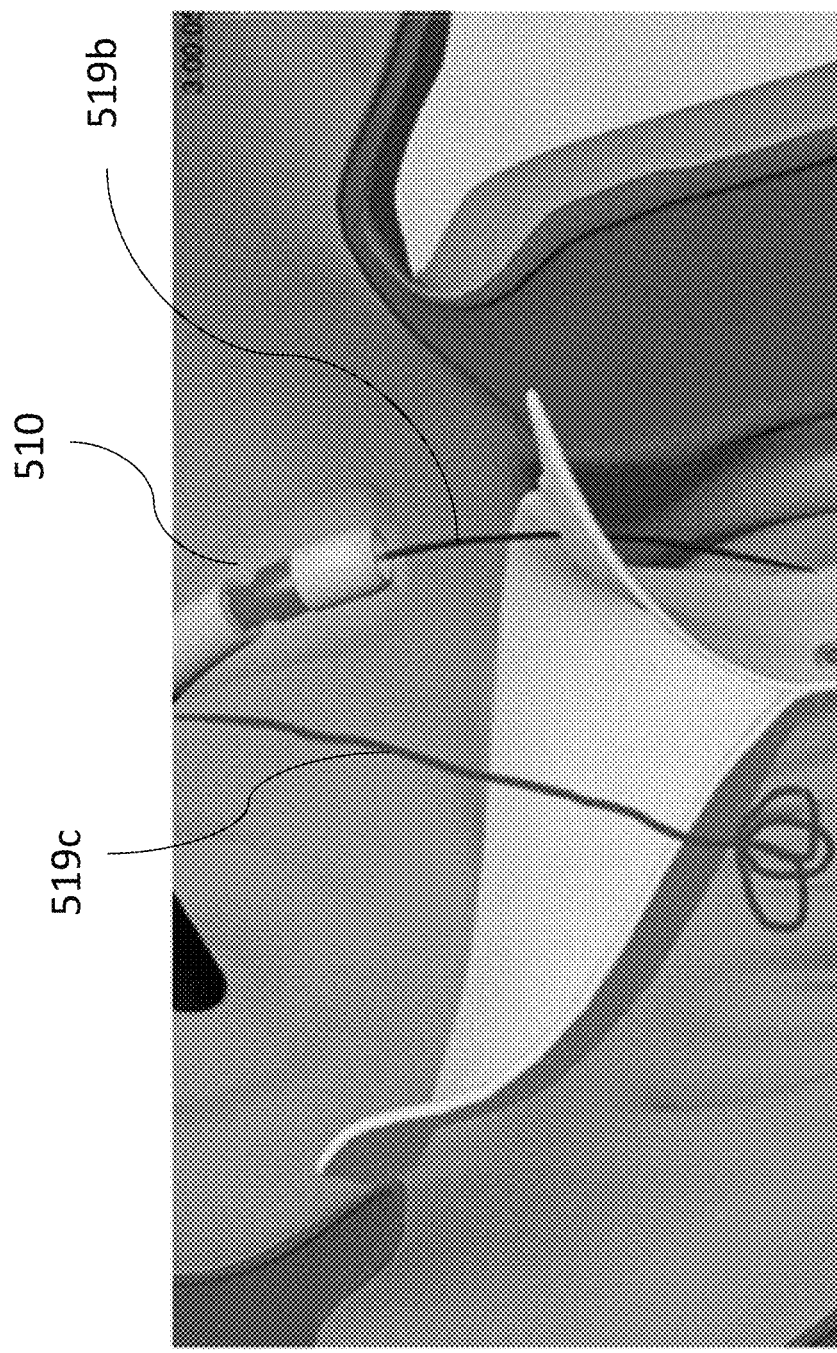
FIG. 28 shows an embodiment of a method of using the improved transseptal puncture system for MitraClip™ or other mitral repair prosthesis device removal.

With reference now to FIG. 28, shown is an embodiment of a method of using the improved transseptal puncture system 500 for MitraClip or other mitral repair prosthesis device removal. Embodiments of this method may use a technique similar to placing the positioning balloon against the mitral valve. Here, the positioning balloon 510 may be placed against a prosthesis like the MitraClip which is now forming double orifices of the mitral valve with the radiofrequency wire 519b being advanced via one of the orifices into the left ventricle. The wire snared via a side port catheter or wire 519c which is advanced into the left ventricle via the adjacent orifice thereby forms a reel from the left atrium into the left ventricle and back into the left atrium such as to snare the MitraClip or other percutaneous mitral repair devices. Using radiofrequency wire, the anterior mitral leaflet is then lacerated right next to the repair device such as to cause an iatrogenic single leaflet detachment. The method described herein could be repeated with the posterior aspect and including the posterior mitral leaflet.

The MitraClip device or a similar mitral repair device would be held in place with a snare or other holding devices such as an alligator clip which may be mechanical or may have magnetic properties so as to prevent embolization of the MitraClip or other repair device. Once the repair device is free, the clip may be retrieved back into the positioning balloon guiding catheter and removed from the body.

Figure 29:
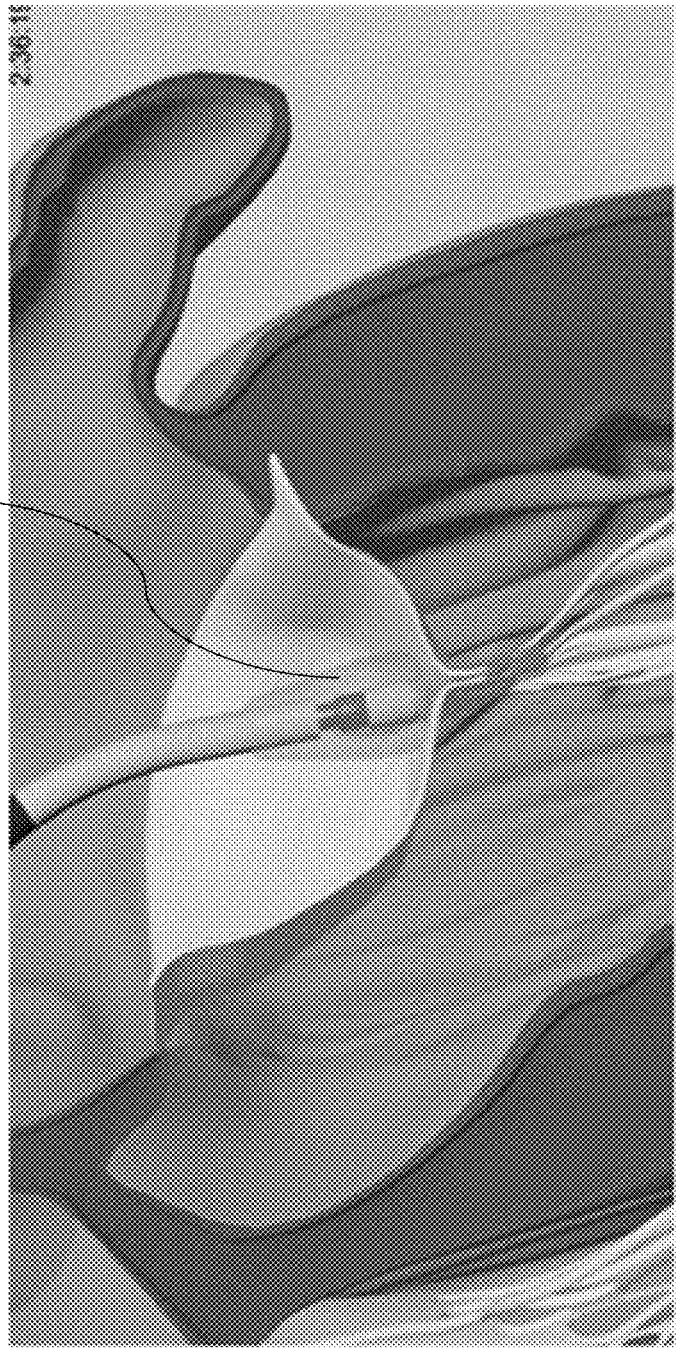
FIG. 29 shows an embodiment of a method of using the improved transseptal puncture system for laceration of a bioprosthetic valve leaflet.

With reference now to FIG. 29, shown is an embodiment of a method of using the improved transseptal puncture system 500 for laceration of a bioprosthetic valve leaflet. The positioning balloon 510 is placed into the base of the bioprosthetic valve leaflet using a radiofrequency puncture member 515 and a radiofrequency capable wire or a radiofrequency wire which is advanced through the bioprosthetic valve leaflet. A snare catheter over wire is then advanced via the guiding catheter to a separate hole through the orifice of the bioprosthetic valve into the adjacent chamber. The radiofrequency wire which was advanced through the bioprosthetic valve leaflet is then snared by the snare catheter wire, thereby forming a loop or radial with the snared radiofrequency wire. Using radiofrequency energy, the bioprosthetic leaflet is then lacerated.

Figure 30:
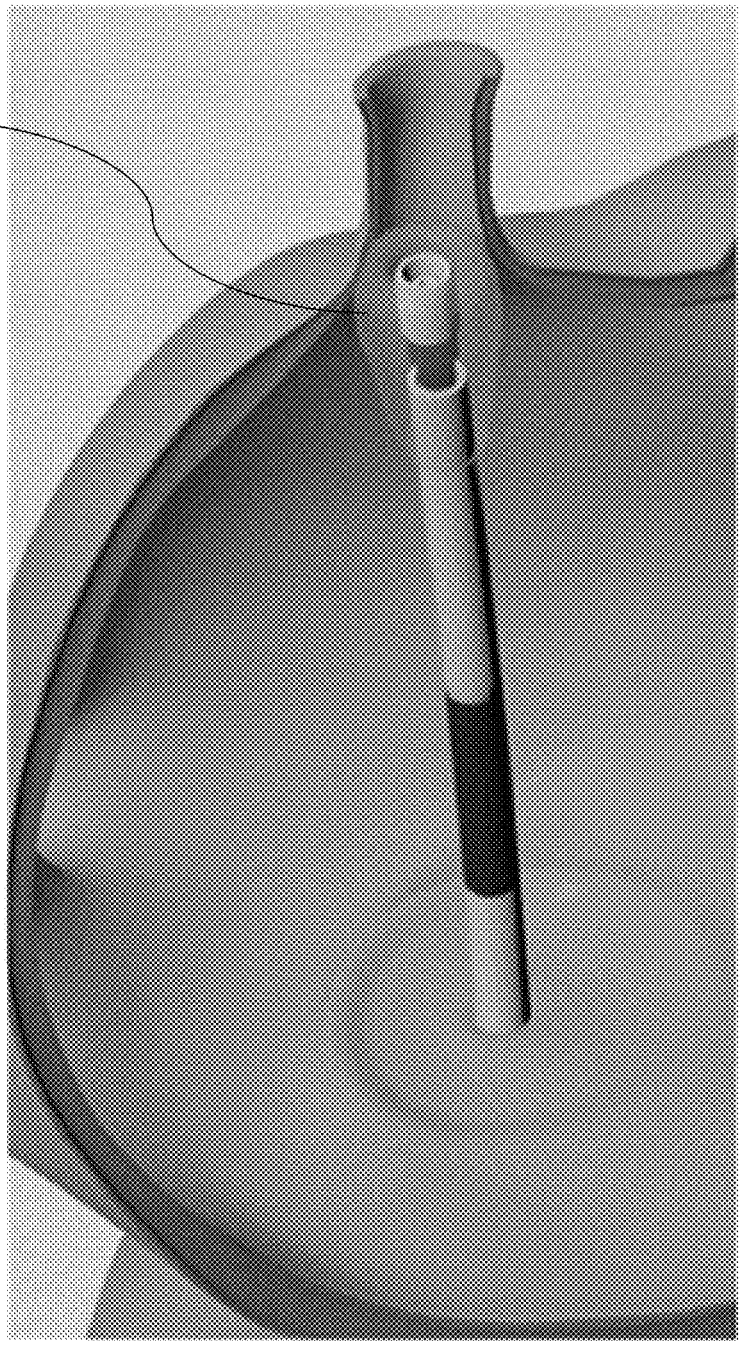
FIG. 30 shows an embodiment of a method of using the improved transseptal puncture system wherein the system anchors in the pulmonary veins, performs pulmonary venous angioplasty, and deliver either radiofrequency heat energy or cryo-energy.
Figures 31A, 31B:
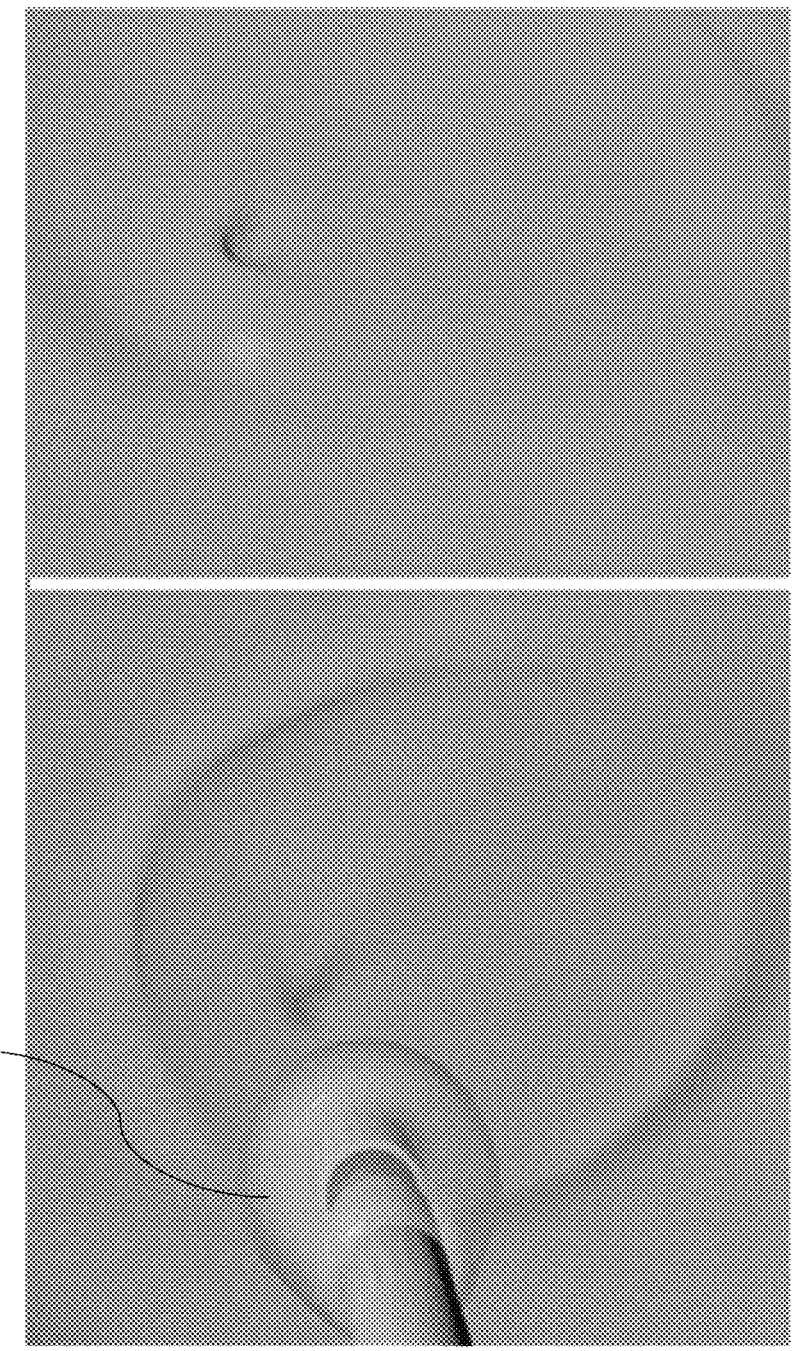
FIGS. 31A-31B and 32A-32B show an embodiment of a method of using the improved transseptal puncture system in which the positioning balloon anchors in the patent foramen *ovale* and identify multiple small atrial septal defects in a cribriform atrial septal defect.
Figures 32A, 32B:
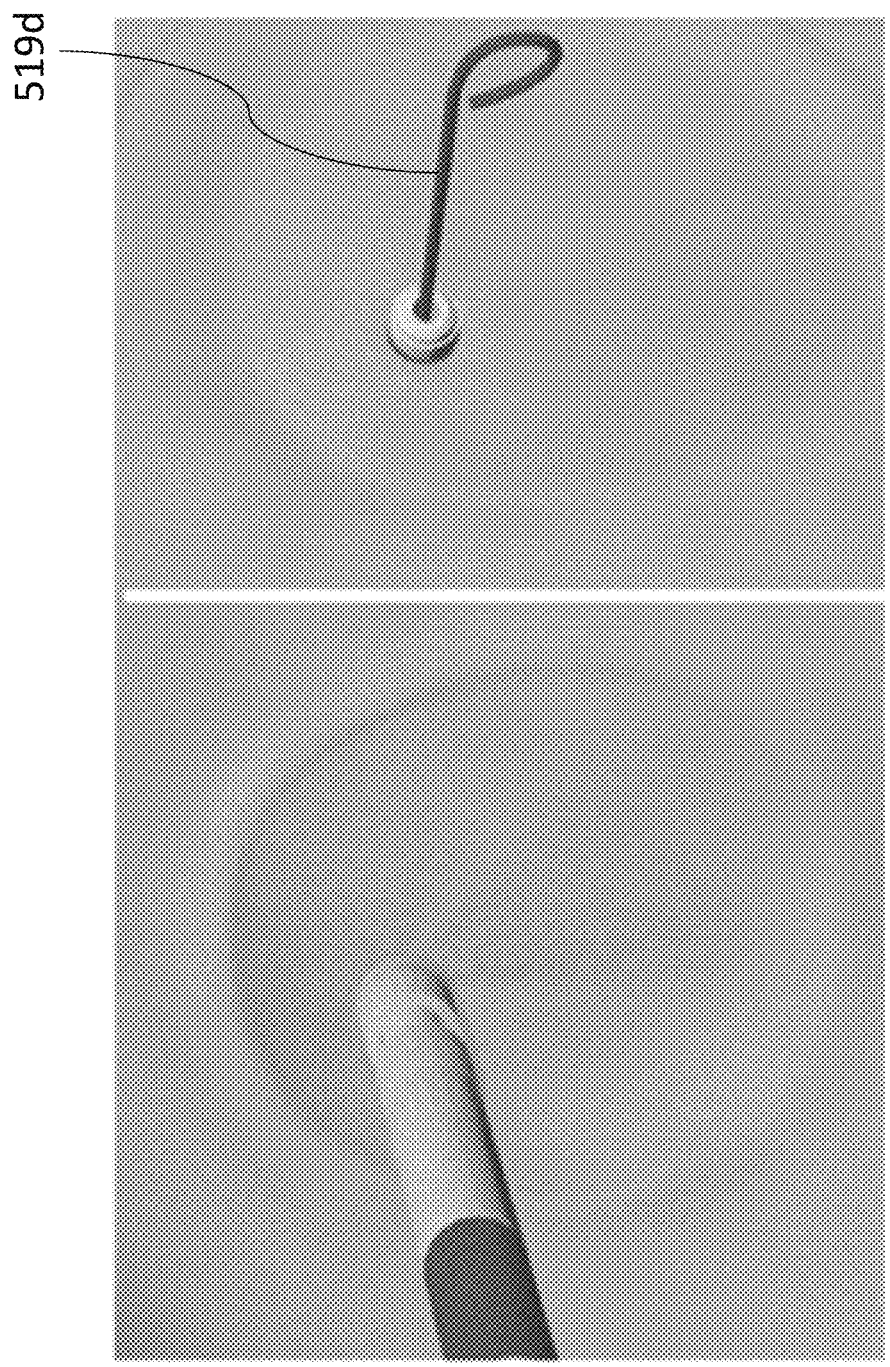

With reference now to FIG. 30, shown is an embodiment of a method of using the improved transseptal puncture system 500 wherein the system anchors in the pulmonary veins, performs pulmonary venous angioplasty, and deliver either radiofrequency heat energy or cryo-energy. In embodiments, the positioning balloon 510 is used to navigate into the pulmonary veins for anchoring purposes as well as to deliver other therapeutic catheters into the pulmonary veins, such as ablation catheters. The positioning balloon 510 may also be used for balloon angioplasty of the pulmonary veins. The positioning balloon 510 may also be used itself to deliver energy in the form of heat or used for cryoablation with the use of products such as liquid nitrogen which could be circulated through the balloon via hypotubes from the outside.

With reference now to FIGS. 31A-32B, shown is an embodiment of a method of using the improved transseptal puncture system 500 in which the positioning balloon 510 anchors in the patent foramen *ovale* and identify multiple small atrial septal defects in a cribriform atrial septal defect. The positioning balloon 510 may be positioned against the fossa from the right atrium and navigated to a patent foramen *ovale* or identify multiple small atrial septal defects in a cribriform atrial septal defect such that a patent foramen *ovale* or small atrial septal defects in a cribriform atrial septal defect could be easily be traversed with a wire with a stable catheter.

Other embodiments include methods of using the improved transseptal puncture system to deliver occluder devices. The positioning balloon shaft may also be used as a delivery guiding catheter for delivering closure devices 519d including atrial septal defect occluder devices, patent foramen *ovale* closure devices, patent ductus arteriosus, paravalvular leak closure devices etc.

Figure 33:
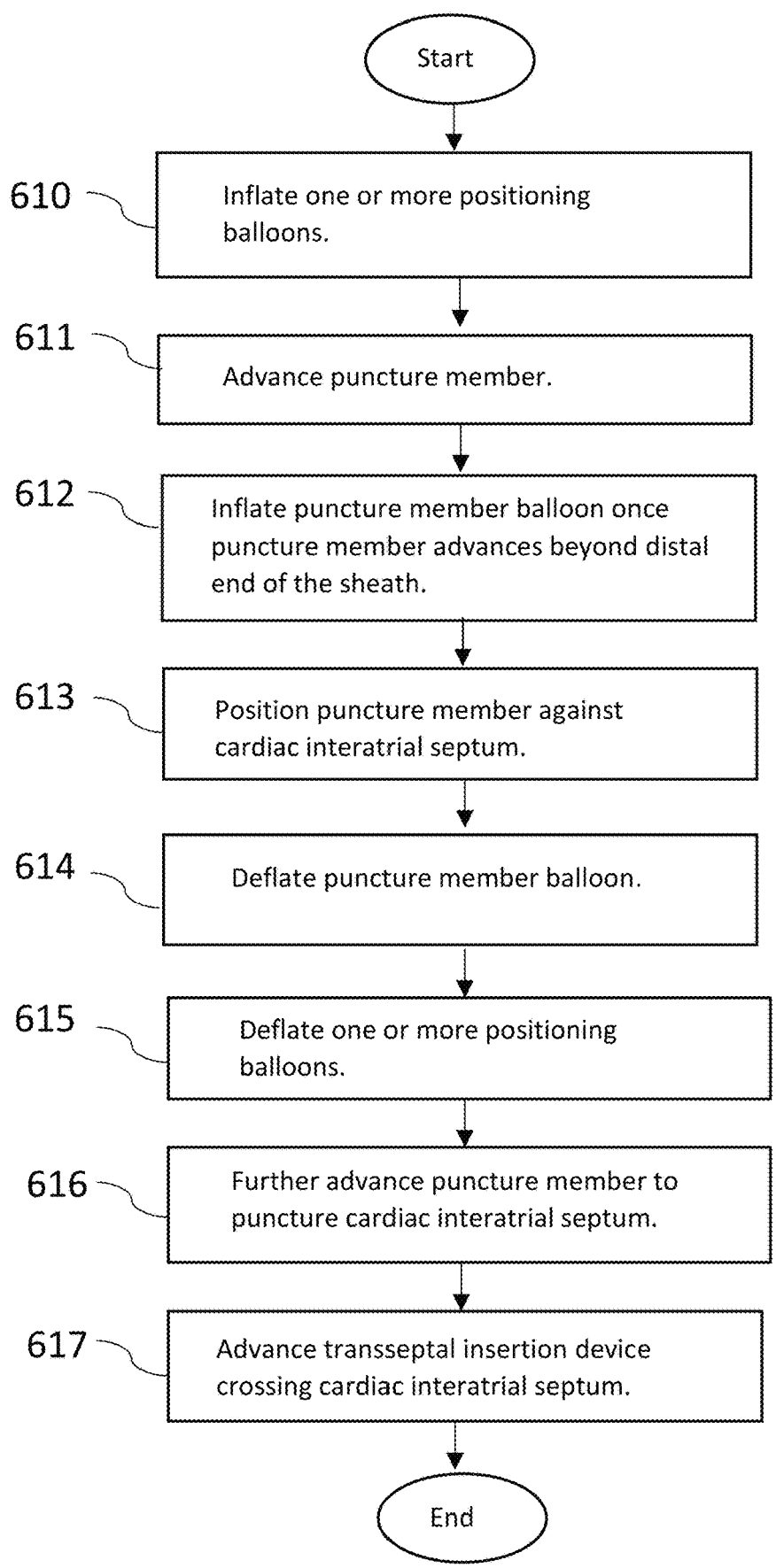
FIG. 33 is a workflow diagram for a method for suitably facilitating precise and safe transseptal puncture of a cardiac interatrial septum with a transseptal insertion device.

With reference to FIG. 33, shown is a workflow diagram for a method 600 for suitably facilitating precise and safe transseptal puncture of a cardiac interatrial septum with a transseptal insertion device 500. One or more positioning balloons 510, which are connected to a distal end of a sheath 514 of the transseptal insertion device, are inflated, block 610. The puncture member 515 while the positioning balloons are inflated is advanced toward cardiac interatrial septum, block 611. The puncture member balloon 504 is inflated, once the puncture member 515 advances beyond the distal end of the sheath 514 and is tenting the cardiac interatrial septum, block 612. The puncture member 515 is positioned against the cardiac interatrial septum, block 613. The puncture member balloon 504 is pressing against the cardiac interatrial septum while the puncture member 515 is tenting the cardiac interatrial septum. The puncture member balloon 504 is deflated, block 614, and the one or more positioning balloons 510 are deflated, block 615, before the puncture member further advances to puncture the cardiac interatrial septum. Then, the puncture member 515 advances to puncture the cardiac interatrial septum, block 616. The transseptal insertion device 500 advances crossing the cardiac interatrial septum, block 617.

Since many modifications, variations, and changes in detail can be made to the described preferred embodiments of the invention, it is intended that all matters in the foregoing description and shown in the accompanying drawings be interpreted as illustrative and not in a limiting sense. Consequently, the scope of the invention should be determined by the appended claims and their legal equivalents.

What is claimed is:

1. A method for suitably facilitating precise and safe transseptal puncture of a cardiac interatrial septum with a transseptal insertion device to perform an intracardiac medical procedure comprising:
providing a transseptal insertion device having a sheath with a distal end, a proximal end, and a lumen extending between the distal and proximal ends and having a positioning balloon extending radially outwardly from the sheath adjacent the sheath distal end wherein the positioning balloon is moveable from an inflated position to a deflated position wherein, in the inflated position, the positioning balloon overhangs and extends past the distal end of the sheath preventing accidental puncturing of the cardiac interatrial septum and stabilizing the transseptal insertion device against fossa ovalis of the cardiac interatrial septum, and wherein a puncture member extends within the sheath lumen and is movable from a retracted position wherein the distal end of the puncture member is within the sheath lumen to an operative position wherein the distal end of the puncture member extends distally from the distal end of said sheath, wherein the puncture member includes a puncture member balloon extending radially outwardly from the puncture member adjacent the distal end of the puncture member wherein the puncture member balloon is moveable from a deflated position to an inflated position;
positioning the puncture member in the retracted position within the sheath;
positioning the transseptal insertion device distal end adjacent a first side of the septum;
inflating the positioning balloon to the inflated position so as to extend past and overhang the sheath distal end;
tenting a surface portion of the first side of the septum with the inflated positioning balloon intended for piercing by the puncture member;
advancing the puncture member within the sheath lumen from the retracted position to the operative position so as to contact the first side of the septum within the inflated positioning balloon;
inflating the puncture member balloon prior to the puncture member contacting the septum;
further advancing the puncture member and contacting the septum;
further advancing the puncture member and piercing the septum;
deflating the positioning balloon;
advancing the transeptal device across the septum; and
reinflating the positioning balloon beyond a second side of the septum for navigating in an atraumatic fashion to different parts of the left atrium for performing the intracardiac medical procedure; and
deflating the puncture member balloon to advance the puncture member prior to said step of advancing the puncture member to the operative position wherein the puncture member balloon is distally positioned relative to the sheath distal end.

2. The method according to claim 1 further comprising the step of deflating the puncture member balloon after said step of piercing the septum.

3. The method according to claim 2 wherein said method further includes the step of removing the puncture member from the sheath lumen.

4. The method according to claim 1 wherein said steps of inflating and deflating the positioning balloon and said steps of inflating and deflating the puncture member balloon occur independent of one another.

5. The method according to claim 1 wherein said step of piercing the septum by the puncture member includes providing an energy source to the puncture member distal tip.

6. The method according to claim 1 wherein the puncture member includes a center lumen and said method further comprises the step of advancing a transseptal wire within said puncture member lumen to advance to the second side of the septum after said step of reinflating the positioning balloon on the second side of the septum.

7. The method according to claim 1 wherein said step of reinflating the positioning balloon includes anchoring the transseptal insertion device against the septum second side by applying proximal tension to the device.

8. The method according to claim 1 wherein said method further comprises the step of removing the puncture member from the sheath lumen and utilizing the sheath lumen as a delivery catheter and advancing a medical device along the sheath lumen to advance to the second side of the septum.

9. The method according to claim 1 further comprising the step of advancing the puncture member beyond said sheath lumen and performing a second piercing step on the second side of the septum.

10. A method for suitably facilitating precise and safe transseptal puncture of a cardiac interatrial septum with a transseptal insertion device to perform an intracardiac medical procedure comprising:
providing a transseptal insertion device having a sheath with a distal end, a proximal end, and a lumen extending between the distal and proximal ends and having a positioning balloon extending radially outwardly from the sheath adjacent the sheath distal end wherein the positioning balloon is moveable from an inflated position to a deflated position wherein, in the inflated position, the positioning balloon overhangs and extends past the distal end of the sheath preventing accidental puncturing of the cardiac interatrial septum and stabilizing the transseptal insertion device against fossa ovalis of the cardiac interatrial septum, and wherein a puncture member extends within the sheath lumen and is movable from a retracted position wherein the distal end of the puncture member is within the sheath lumen to an operative position wherein the distal end of the puncture member extends distally from the distal end of said sheath, wherein the sheath defines an inflation port positioned adjacent the positioning balloon, and wherein the puncture member includes a puncture member balloon extending radially outwardly from the puncture member adjacent the distal end of the puncture member wherein the puncture member balloon is moveable from a deflated position to an inflated position
positioning the puncture member in the retracted position within the sheath;
positioning the transseptal insertion device distal end adjacent a first side of the septum;
providing fluid communication between the positioning balloon and the sheath lumen;
inflating the positioning balloon to the inflated position using said inflation port so as to extend past and overhang the sheath distal;
tenting a surface portion of the first side of the septum with the inflated positioning balloon intended for piercing by the puncture member;
advancing the puncture member within the sheath lumen from the retracted position to the operative position so as to contact the first side of the septum within the inflated positioning balloon,
inflating the puncture member balloon prior to the puncture member contacting the septum and wherein inflating the puncture member balloon includes positioning the puncture member balloon within the sheath lumen and occluding the inflation port thereby permitting the positioning balloon to remain in the inflated position;
further advancing the puncture member and contacting the septum;
further advancing the puncture member and piercing the septum;
deflating the positioning balloon using said inflation port;
advancing the transeptal device across the septum;
reinflating the positioning balloon using said inflation port beyond a second side of the septum for navigating in an atraumatic fashion to different parts of the left atrium for performing the intracardiac medical procedure.

11. The method according to claim 10 wherein said step of advancing the puncture member for piercing the septum includes positioning the puncture member balloon distal to the inflation port to deflate the positioning balloon in said step of deflating the positioning balloon.

12. A method for suitably facilitating precise and safe transseptal puncture of a cardiac interatrial septum with a transseptal insertion device to perform an intracardiac medical procedure comprising:
providing a transseptal insertion device having a sheath with a distal end, a proximal end, and a lumen extending between the distal and proximal ends and having a positioning balloon extending radially outwardly from the sheath adjacent the sheath distal end wherein the positioning balloon is moveable from an inflated position to a deflated position wherein, in the inflated position, the positioning balloon overhangs and extends past the distal end of the sheath preventing accidental puncturing of the cardiac interatrial septum and stabilizing the transseptal insertion device against fossa ovalis of the cardiac interatrial septum, and wherein a puncture member extends within the sheath lumen and is movable from a retracted position wherein the distal end of the puncture member is within the sheath lumen to an operative position wherein the distal end of the puncture member extends distally from the distal end of said sheath, wherein the puncture member includes a puncture member balloon extending radially outwardly from the puncture member adjacent the distal end of the puncture member wherein the puncture member balloon is moveable from a deflated position to an inflated position;
positioning the puncture member in the retracted position within the sheath;
positioning the transseptal insertion device distal end adjacent a first side of the septum;
inflating the positioning balloon to the inflated position so as to extend past and overhang the sheath distal end;
tenting a surface portion of the first side of the septum with the inflated positioning balloon intended for piercing by the puncture member;
advancing the puncture member within the sheath lumen from the retracted position to the operative position so as to contact the first side of the septum within the inflated positioning balloon;
further advancing the puncture member and contacting the septum;

further advancing the puncture member and piercing the septum;
deflating the positioning balloon;
advancing the transeptal device across the septum; and
reinflating the positioning balloon beyond a second side of the septum for navigating in an atraumatic fashion to different parts of the left atrium for performing the intracardiac medical procedure,
wherein the puncture member balloon is positioned a predetermined distance from a tip of the distal end of the puncture member and the inflated puncture member balloon abuts against the first side of the septum and prevents the puncture member from being pushed beyond the predetermined distance during said step of piercing the septum by the puncture member.

* * * * *